United States Patent
Smartt et al.

(10) Patent No.: US 6,365,873 B1
(45) Date of Patent: Apr. 2, 2002

(54) APPARATUS FOR THE CONCURRENT INSPECTION OF PARTIALLY COMPLETED WELDS

(75) Inventors: Herschel B. Smartt; John A. Johnson; Eric D. Larsen, all of Idaho Falls; Rodney J. Bitsoi, Ririe; Ben C. Perrenoud, Rigby; Karen S. Miller; David P. Pace, both of Idaho Falls, all of ID (US)

(73) Assignee: Bechtel BWXT Idaho, LLC, Idaho Falls, ID (US)

( * ) Notice: Subject to any disclaimer, the term of this patent is extended or adjusted under 35 U.S.C. 154(b) by 0 days.

(21) Appl. No.: 09/583,632

(22) Filed: May 31, 2000

Related U.S. Application Data

(60) Provisional application No. 60/137,045, filed on Jun. 1, 1999.

(51) Int. Cl.[7] ................................................. B23K 9/095
(52) U.S. Cl. ................................... 219/130.01; 228/104
(58) Field of Search ........................ 219/130.01, 130.21, 219/124.34; 228/104; 73/598, 620, 622, 624

(56) References Cited

U.S. PATENT DOCUMENTS

| | | | | |
|---|---|---|---|---|
| 3,575,042 A | * | 4/1971 | Lovelace et al. | 73/620 |
| 3,712,119 A | * | 1/1973 | Cross et al. | 73/624 |
| 4,144,766 A | * | 3/1979 | Wehrmeister | 228/104 |
| 4,375,165 A | * | 3/1983 | Sterke | 73/622 |
| 4,588,873 A | * | 5/1986 | Fenn et al. | 219/124.34 |
| 4,712,722 A | * | 12/1987 | Hood et al. | 228/104 |
| 6,125,705 A | * | 10/2000 | Johnson | 73/598 |

* cited by examiner

*Primary Examiner*—Clifford C. Shaw
(74) *Attorney, Agent, or Firm*—Wells St. John Roberts Gregory & Matkin

(57) ABSTRACT

An apparatus for the concurrent inspection of partially completed welds is described in which is utilized in combination with a moveable welder for forming a partially completed weld, and an ultrasonic generator mounted on a moveable welder in which is reciprocally moveable along a path of travel which is laterally disposed relative to the partially completed weld.

28 Claims, 14 Drawing Sheets

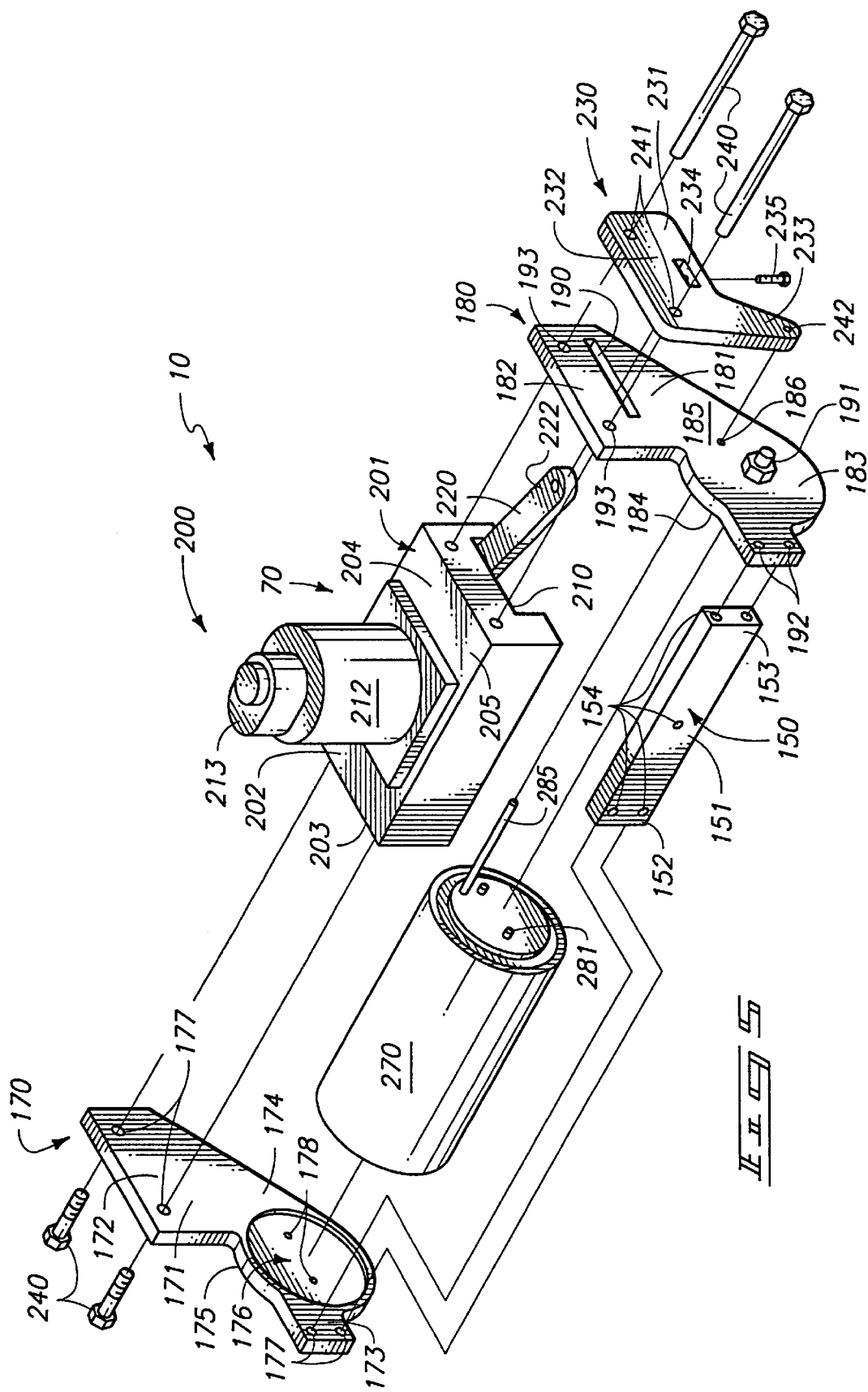

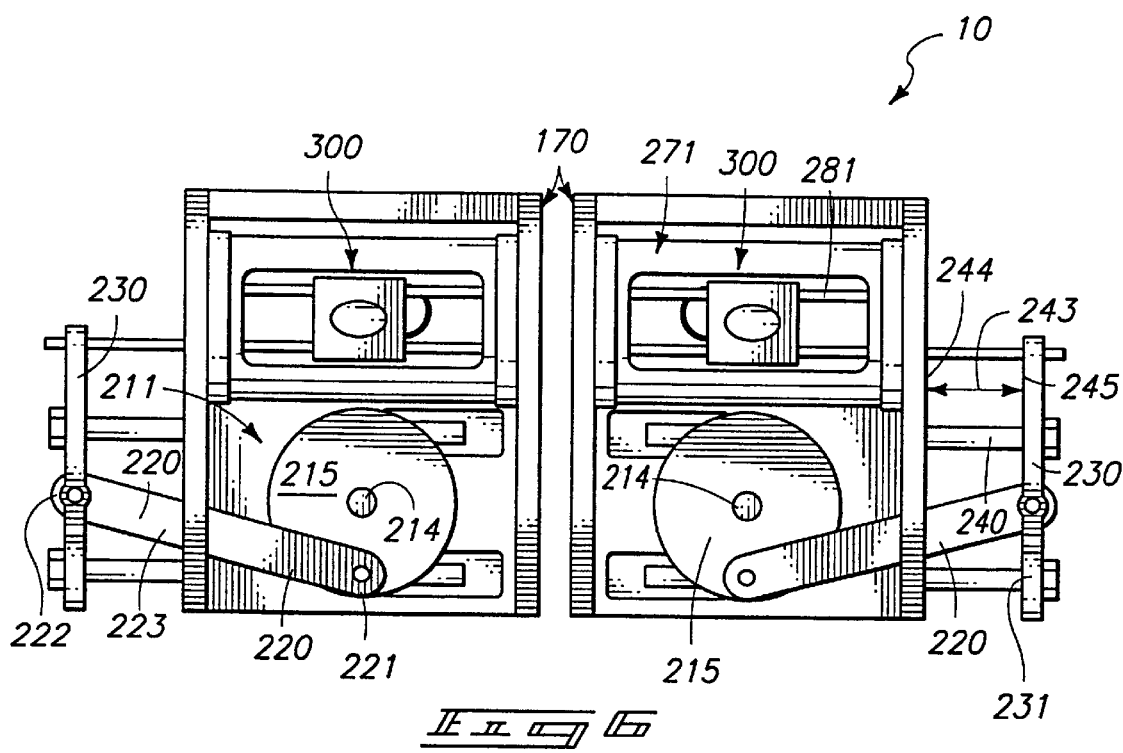
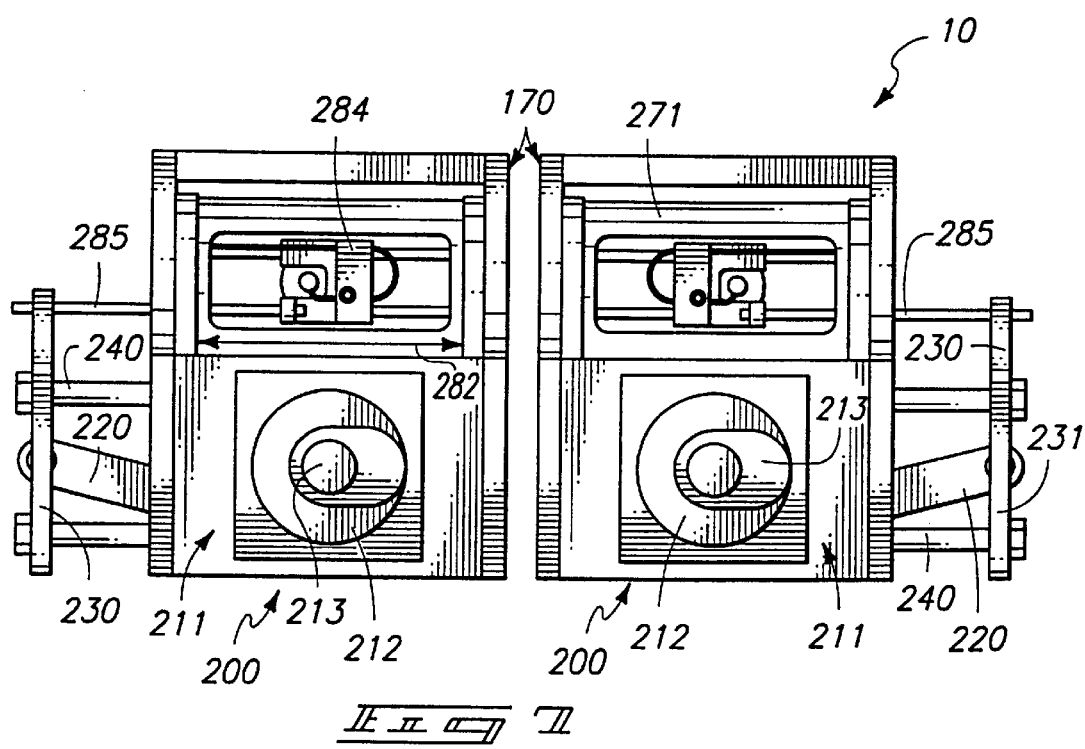

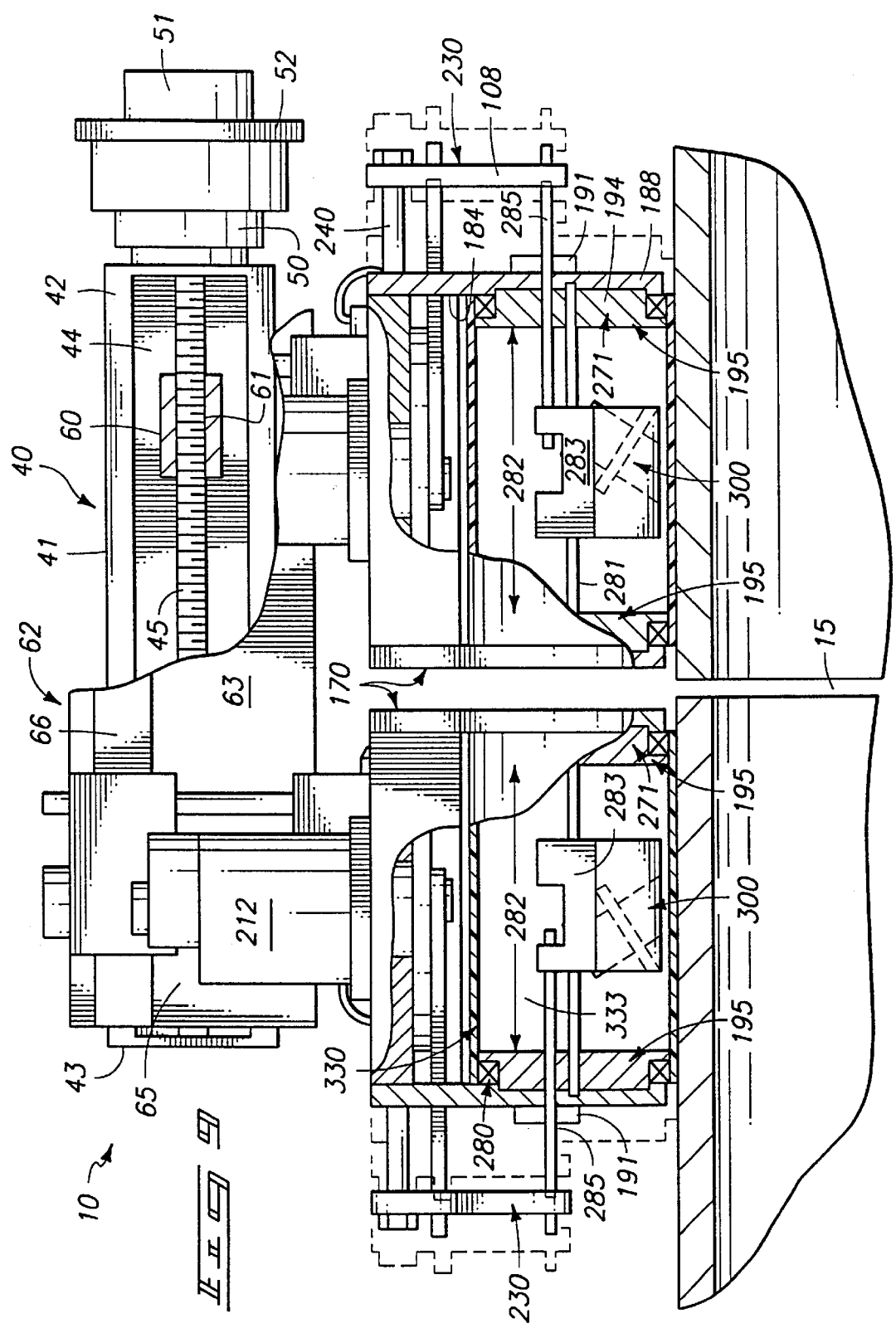

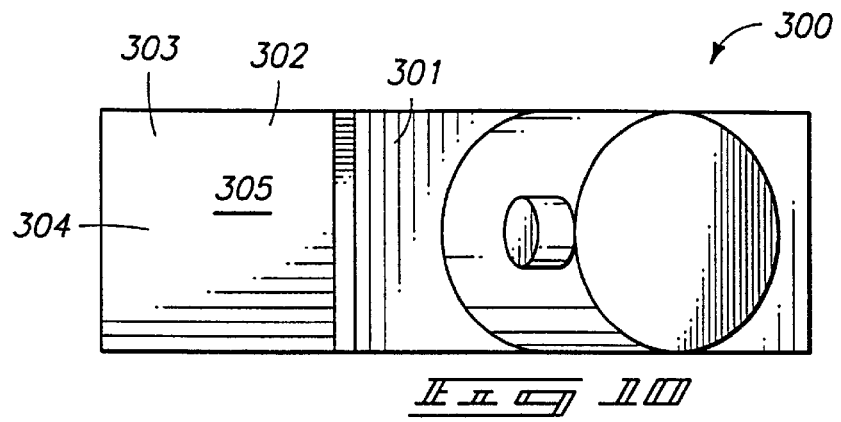
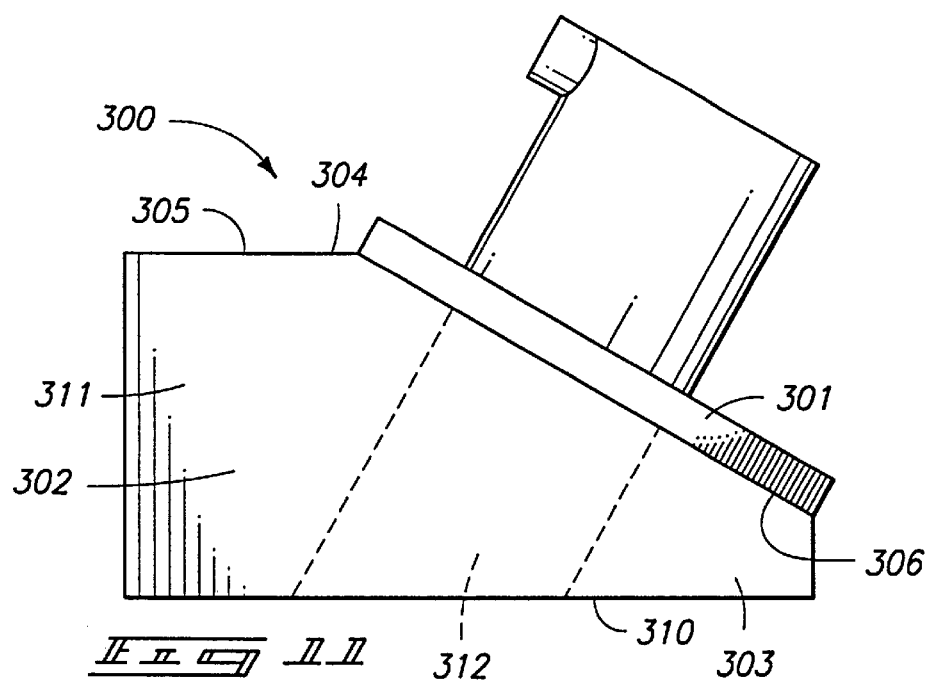
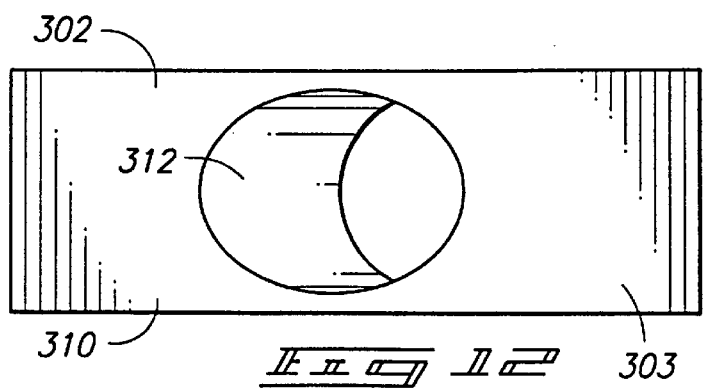

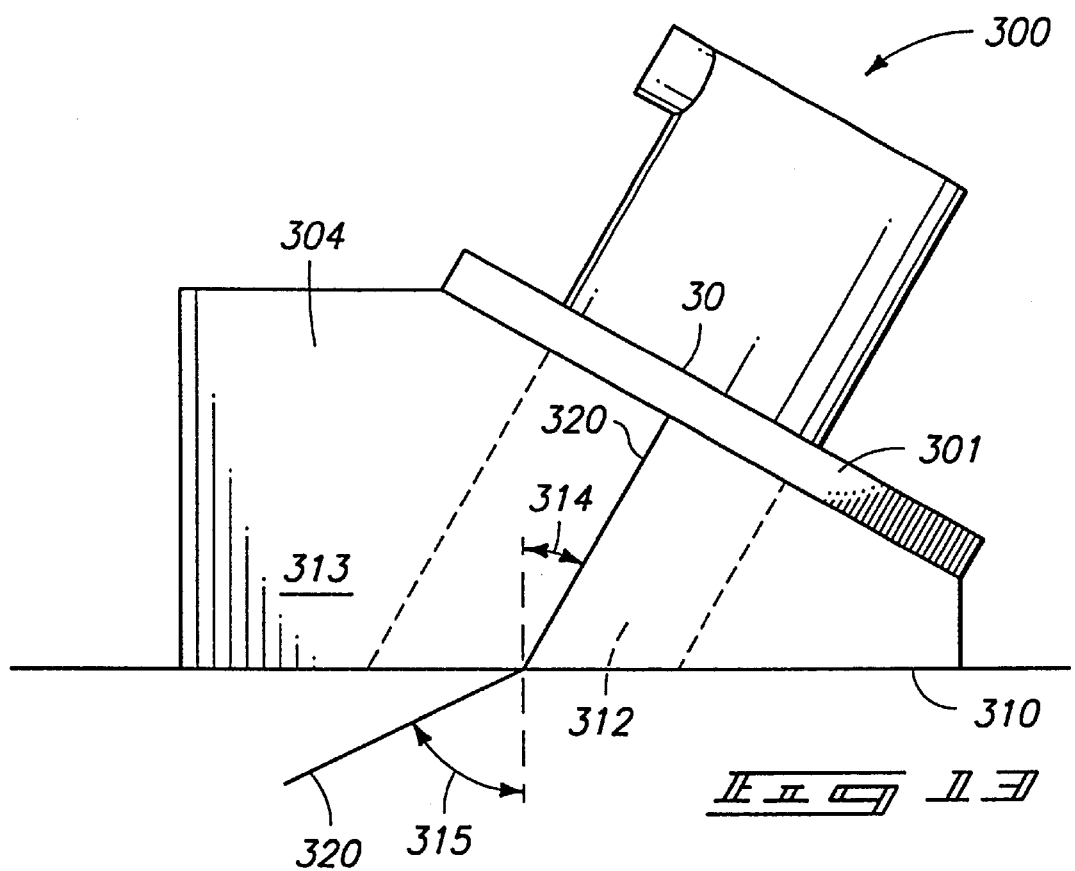

US 6,365,873 B1

APPARATUS FOR THE CONCURRENT INSPECTION OF PARTIALLY COMPLETED WELDS

RELATED APPLICATION

This application claims priority from U.S. provisional application Ser. No. 60/137,045 filed Jun. 1, 1999 and is incorporated by reference.

CONTRACTUAL ORIGIN OF THE INVENTION

This invention was made with United States Government support under Contract No. DE-AC07-94ID13223, now Contract No. DE-AC07-99ID13727 awarded by the United States Department of Energy. The United States Government has certain rights in the invention.

FIELD OF THE INVENTION

The present invention relates to an apparatus which facilitates the concurrent nondestructive evaluation of partially completed welds.

BACKGROUND OF THE INVENTION

Various welding devices are utilized for joining metal substrates together under various operational and environmental conditions. For example, ultrasonic sensors may be located generally laterally outwardly relative to the opposite sides of a partially completed weld such that a completed weld may be thoroughly inspected to determine the presence of assorted welding flaws. In the event that the welding flaws are detected, corrective action is taken to correct the flaw, and then welding operations are started again. This inspection technique greatly facilitates the successful completion of welding operations, while simultaneously reducing the cost of conducting same by substantially reducing time delays normally associated in correcting flaws detected late in the welding process. For example, in the prior art, if a flaw is detected in an area of the given weld once the welding device has passed several times over the same area, significant time delays and expenses are experienced as workers remove the overlying welding material, as by grinding or the like, to uncover the flaw and correct same.

However, the inventors of the apparatus have discovered that for inspection of the welds to be accurate, the movement of ultrasonic sensors must be synchronized, within small tolerance parameters.

In view of the foregoing, it would be highly desirable to provide a method and apparatus for the concurrent inspection of partially completed welds which achieves the benefits to be derived from the aforementioned technology, but which avoids the detriments individually associated therewith.

OBJECTS AND SUMMARY OF INVENTION

Therefore, one aspect of the present invention is to provide an improved inspection apparatus for evaluating a partially completed weld.

Another aspect of the present invention is to provide an inspection apparatus which includes a moveable welder for forming a partially completed weld, which, in one form of the invention, includes an ultrasonic generator mounted on the moveable welder and which is reciprocally moveable along a path of travel which is laterally disposed relative to the partially completed weld.

Another aspect of the present invention is to provide an inspection apparatus which includes a propulsion assembly disposed driving relation relative to the ultrasonic generator to reciprocally move the ultrasonic generator along the path of travel, and wherein the path of travel is substantially normal to the partially completed weld.

Another aspect of the present invention is to provide an inspection apparatus which includes an adjustment assembly borne by the moveable welder and which is operable to selectively alter the position of the path of travel of the ultrasonic generator relative to the partially completed weld.

Another aspect of the present invention is to provide an inspection apparatus which includes a location sensor, which in one form of the invention, determines the location of the ultrasonic generator as it moves along the path of travel, and wherein the ultrasonic generator concurrently generates ultrasonic signals during welding operations.

Another aspect of the present invention is to provide an inspection apparatus which includes a hollow sensor wheel assembly, which in one form of the invention, encloses the ultrasonic generator and is disposed in trailing relation relative to the moveable welder, and wherein the path of travel of the ultrasonic generator is located within the hollow sensor wheel assembly.

Another aspect of the present invention is to provide an inspection apparatus which includes an ultrasonic wedge, which in one form of the invention, is oriented in ultrasonic signal receiving relation relative to the ultrasonic generator, and wherein the ultrasonic wedge moves in unison with the ultrasonic generator along the path of travel.

These and other aspects of the invention will be discussed hereinafter.

BRIEF DESCRIPTION OF THE DRAWINGS

Preferred embodiments of the invention are described below with reference to the following accompanying drawings.

FIG. 5 is a partial, exploded, perspective view of one form of the inspection apparatus of the present invention.

FIG. 6 is a partial, bottom, plan view of the inspection apparatus with some surfaces removed to show the structure thereunder.

FIG. 7 is a partial, top, plan view of the inspection apparatus with some surfaces removed to show the structure thereunder.

FIG. 9 is a fragmentary, rear elevation view of an inspection apparatus of the present invention disposed in rolling engagement with a supporting surface.

FIG. 10 is a partial top, plan view of an ultrasonic signal generator/receiver in combination with an ultrasonic wedge, and which is employed with the present invention.

FIG. 11 is a side elevational view of the structure seen in FIG. 10.

FIG. 12 is a bottom plan view of the structure seen in FIG. 10.

FIG. 13 is a side elevational view of the ultrasonic signal generator/receiver and wedge of FIG. 10 and further illustrating an ultrasonic signal transmitted therein and into an adjoining substrate.

DETAILED DESCRIPTION OF THE PREFERRED EMBODIMENTS

Figure 1:
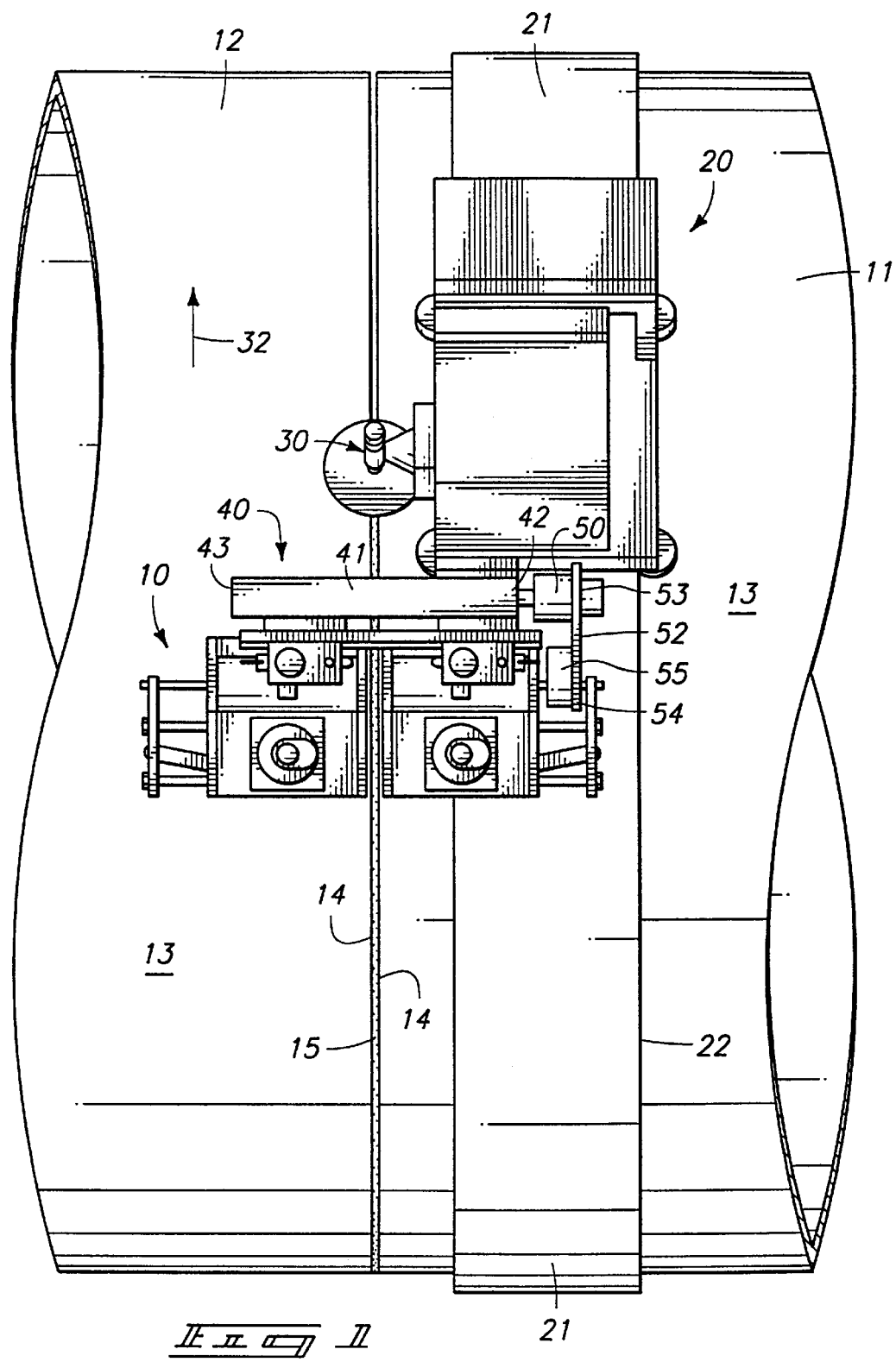
FIG. 1 is a top plan view of one form of the inspection apparatus of the present invention shown in a typical environment and in combination with a moveable welder.
Figure 2:
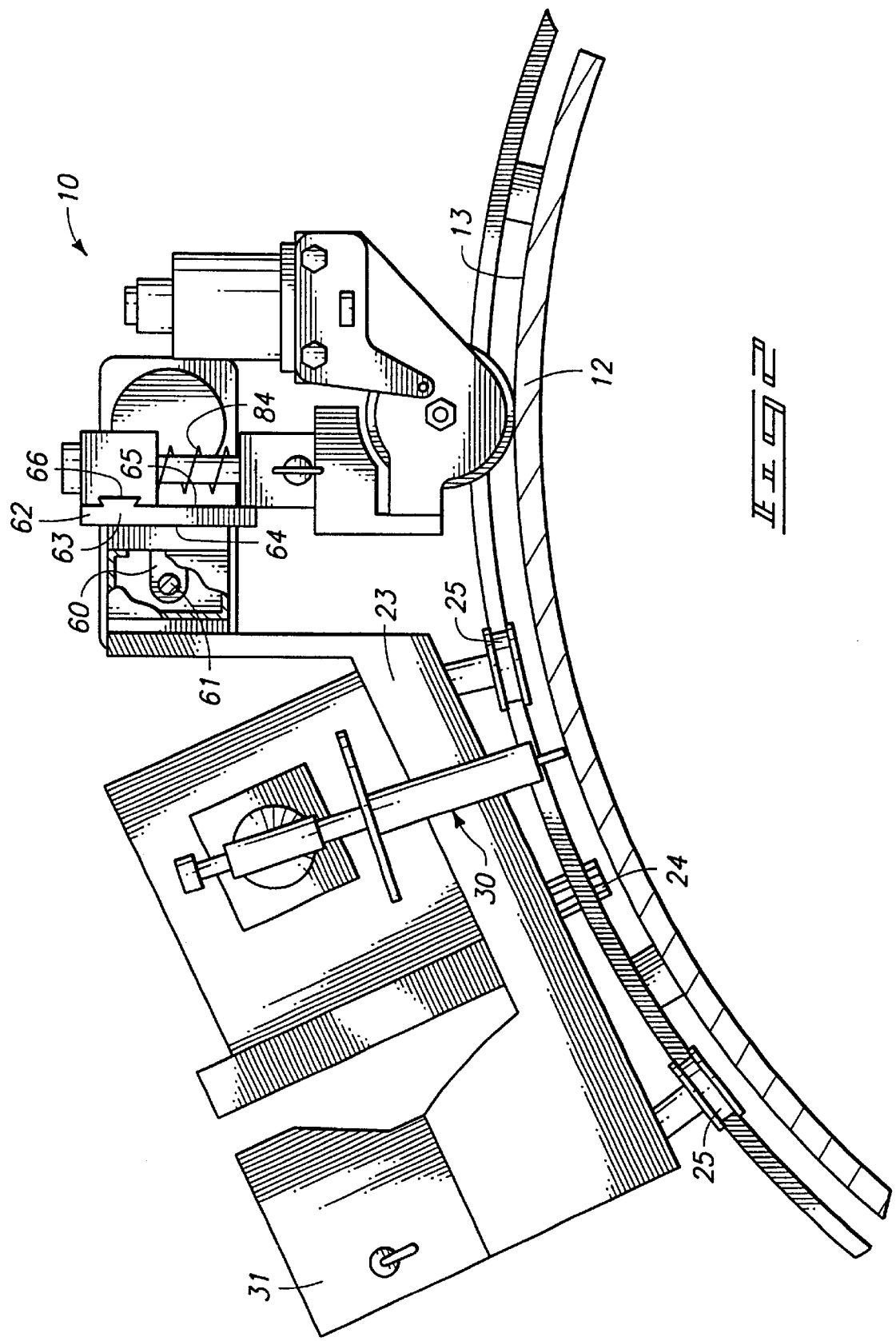
FIG. 2 is a side elevational view of one form of the inspection apparatus of the present invention.

This disclosure of the invention is submitted in furtherance of the constitutional purpose of the U.S. Patent Laws to promote the progress of science in the useful arts [Article 1 §8, first paragraph]. The apparatus for the concurrent inspection of partially completed welds is best seen in the environmental views of FIGS. 1 and 2, and is generally indicated by the numeral 10. In the environmental views as seen in FIGS. 1 and 2, the apparatus 10 of the subject invention is operable to move along first and second pipes generally designated by the numerals 11 and 12. Each pipe is defined by a supporting surface 13. Further, each of the supporting surfaces have a peripheral edge 14 which defines therebetween a partially completed weld, which is generally designated by the numeral 15. As seen in FIGS. 1 and 2, a moveable welder is generally designated by the numeral 20, and is operable to move along the supporting surfaces 13 for purposes of welding the first and second pipes 11 and 12 together. The moveable welder 20 is well known in the art and is operable to move along a rail of track 21 which is fastened on one of the pipes 11 or 12. The moveable welder 20 further includes a carriage 23 which mounts a pinion gear 24 which engages a rack gear [not shown] which is mounted along the peripheral edge 22 of the rail or track 21. Still further, the moveable welder 20 is disposed in rolling engagement with the rail or track 21 by way of wheels 25. As best seen in FIGS. 1 and 2 the moveable welder 20 includes an electric welding torch 30. The automated moveable welder further mounts a control box 31 which controls the operations of the moveable welder. As best seen in the plan view of FIG. 1, the moveable welder 20 moves along a path of travel which is generally indicated by the numeral 32 and which is substantially parallel to the partially completed weld 15.

As best seen by reference to FIGS. 1 and 9, the apparatus 10 of the subject invention includes an adjustment assembly generally designated by the numeral 40. The adjustment assembly 40 is borne by the moveable welder 20 and disposed in trailing relation relative thereto. The adjustment assembly 40 includes a guide member which is generally designated by the numeral 41. The guide member 41, as shown in FIG. 9, is narrowly rectangular, and has a first end 42 and an opposite second end 43. The guide member 41 defines a cavity 44 which extends longitudinally thereof, and further a rotatable drive member, here shown as a continuous screw 45, is mounted for rotational movement generally about the longitudinal axis thereof. As seen in FIG. 9, a motor 50 is mounted on the guide member 41 at the first end 42 thereof. Still further, an encoder 51 is disposed in controlling, signal transmitting relation relative to the motor 50. Still further, as seen in the plan view of FIG. 1, and as further shown in FIG. 9, a bracket 52 is mounted on the motor 50 and extends generally rearwardly relative to the path of movement 32 of the moveable welder 20. The bracket 52 has a first end 53, which is mounted on the motor 50, and an opposite second end 54. As seen in the plan view of FIG. 1, a tracking sensor 55 is mounted on the second end 54 of the bracket, and is operable to adjust the position of present apparatus 10 relative to the partially completed weld 15. It should be understood that the motor 50, associated encoder 51 and tracking sensor 55 are each coupled in signal transmitting and receiving relation relative to a controller which will be discussed in greater detail hereinafter. Still further, the adjustment assembly 40 is operable to selectively alter the location of the path of travel of a ultrasonic generator or receiver laterally outwardly relative to the partially completed weld 15. The ultrasonic generator or receiver will be discussed below.

As best seen by reference to FIGS. 1 and 9, the adjustment assembly 40 further includes a mounting fixture 60 which is moveable along the cavity 44 upon rotation of the drive member 45. As will be seen in the partial, sectional view of FIGS. 2 and 9, the moveable mounting fixture 60 includes a threaded bore 61 which is matingly received thereabout the drive member 45. Affixed to the moveable mounting fixture 60 is a mounting plate generally indicated by the numeral 62. The mounting plate 62 has a main body 63 which has an inwardly facing surface 64, which is affixed to the moveable mounting fixture 60, and further an opposite outwardly facing surface 65 which has formed in its surface or made integral therewith a dove-tailed ridge generally indicated by the numeral 66. As will be understood, rotation of the continuous drive member 45, by the motor 50, causes movement of the mounting plate 62 in a direction generally transversely relative to the partially completed weld 15. As seen in FIG. 9, the dove-tailed ridge 66 generally extends along the main body 63 and is disposed in substantially parallel spaced relation relative to the underlying supporting surfaces 13, of the first and second pipes 11 and 12.

Figure 3:
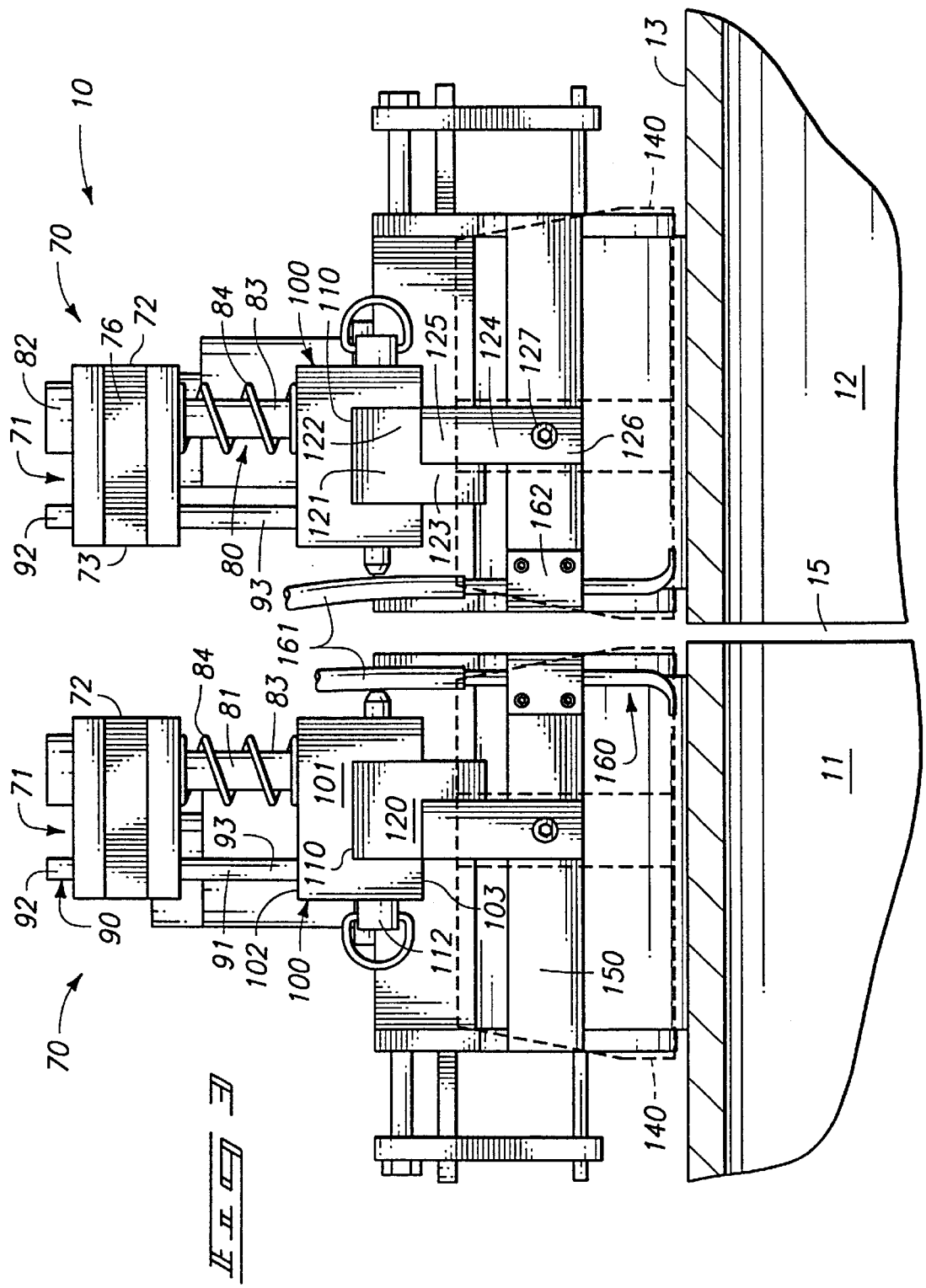
FIG. 3 is a front elevational view of one form of the inspection apparatus of the present invention with the moveable welder removed.
Figure 4:
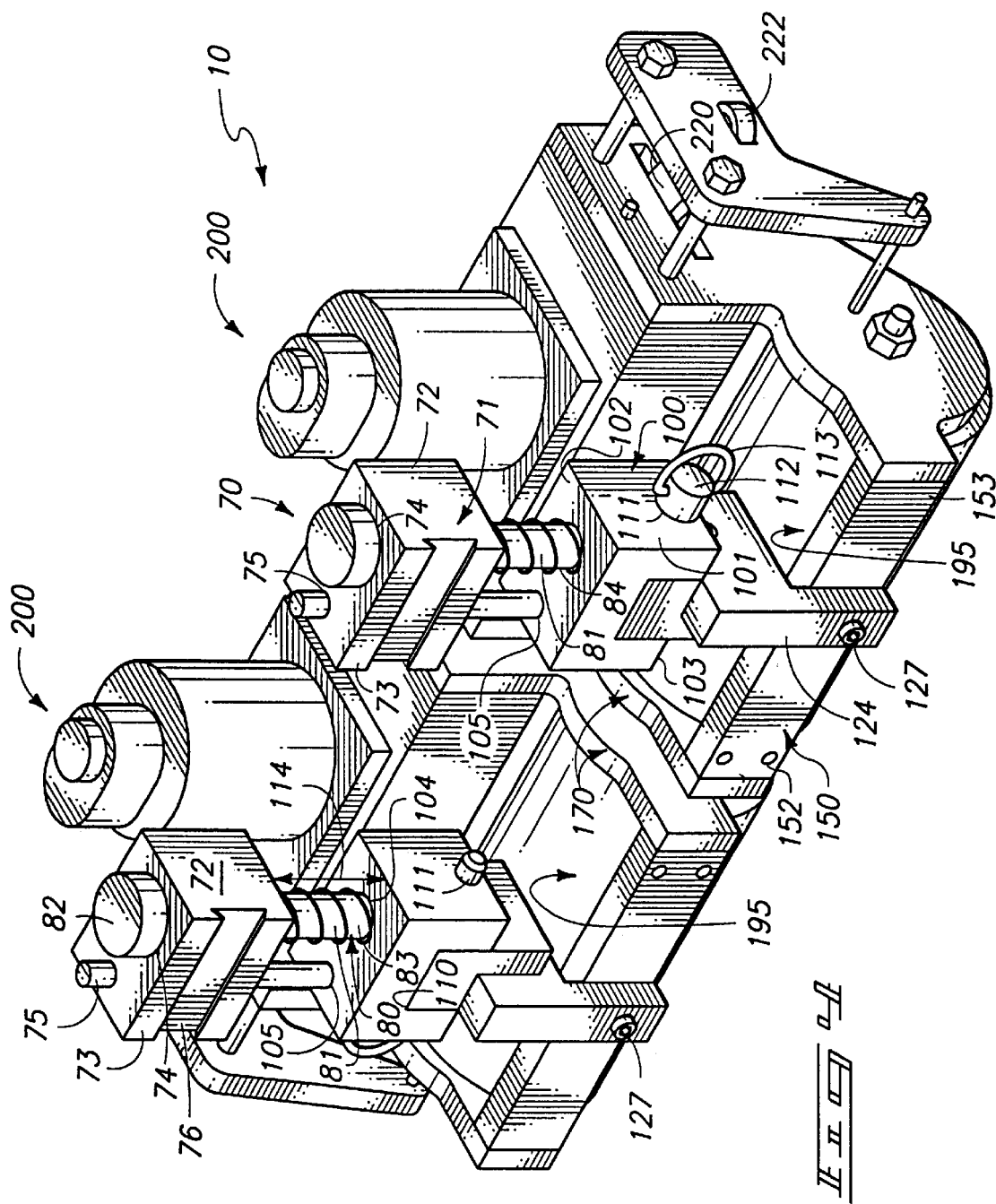
FIG. 4 is a perspective view of one form of the inspection apparatus of the present invention with the moveable welder removed.

As best seen by references to FIGS. 3 and 4, the apparatus 10 of the subject invention has a strut assembly generally designated by the numeral 70. As shown therein the strut assembly 70 includes a first or upper portion designated generally by the numeral 71. The first, or upper portion 71 has a main body designated by the numeral 72, and is further defined by an exterior facing surface 73. As seen in FIG. 4, a first or major aperture or passageway 74, is formed therein, and extends through the main body 72. Still further, a second or minor aperture 75 is also formed in the main body and extends therethrough. As seen in FIG. 4, a dove-tailed groove 76 is formed in the exterior surface 73, and is operable to matingly engage with the dove-tailed ridge 66 which is made integral with the outwardly facing surface 65, of the mounting plate 62. As such, the main body 72 of the upper portion 71 is operable to be slidably moved along the mounting plate 62 into various desired positions.

As best seen by references to FIGS. 3 and 4, the apparatus 10 of the subject invention includes a strut rod generally indicated by the numeral 80, and which is affixed in the first or major aperture or passageway 74 which is defined by the first or upper portion 71. The strut rod has a main body 81 which has a first end 82, received in a fixed relationship in the major aperture 74, and an opposite second end 83 which is remote thereto. Still further, a biasing spring 84 is received about the main body 81 such that the main body 81 is received in telescoping relation relative to the biasing spring 84. Still further, a guide rod, which is generally indicated by the numeral 90, has a main body 91, with a first end 92, which is received in the second or minor aperture 75, and which is affixed to the first or upper portion 71. The guide rod 90 has an opposite second end 93 that is remote thereto. As best seen by a study of FIGS. 3 and 4, the strut assembly 80 includes a lower portion which is generally designated by the numeral 100 and which is moveable relative to the first portion. The lower portion 100 has a main body 101 having an upper or first end 102, and an opposite, lower, or second end 103. As seen in FIG. 4, the lower or second end 103 has a major passageway 104 and a minor passageway 105 formed therein. The major and minor passageways 104 and 105, respectively, are operable to slidably receive the respective second ends 83 and 93 of the strut rod 80 and guide rod 90 respectively. As seen from a study of FIG. 4, the biasing spring 84 imparts force thereagainst the upper or first end 102 and otherwise operates as a shock absorber. Still further, the lower or second end 103 has a channel 110 formed therein. A release pin passageway 111 is formed in the main body 101 and extends therethrough the main body 101. The release pin passageway 111 is disposed generally transversely relative to the channel 110 which is formed in the lower or second end 103. As seen in FIG. 4, a release pin 112 is operable to be releasably matingly received in the release pin passageway 111. The release pin 112 has a handle 113 which allows an operator to grasp the end thereof and remove it from the associated passageway 111. This will result in the apparatus 10 being released from the moveable welder 20. When assembled, and rendered operational, it should be understood that the lower portion 100 of the strut assembly 70 is operable to reciprocally move along a path of travel 114 (FIG. 4) and along the respective strut rod and guide rod 80 and 90 respectively. This allows the apparatus 10 to move over irregular features on the supporting surface 13.

As seen in FIG. 3, a connecting bracket which is generally indicated by the numeral 120, is releasably secured in the channel 110 which is formed in the lower portion 100. The connecting bracket 120 has an L-shaped main body designated by the numeral 121. The L-shaped main body has a first leg 122 which has a channel or passageway formed therein [not shown]. This channel is coaxially aligned with the release pin passageway 111 such that the release pin 112 can be slidably received therein, and thus, releasably secure the connecting bracket 120 to the lower portion 100. A second leg 123 depends downwardly at a substantially normal position relative to the first leg 122. The second leg 123 is secured by means of a fastener [not shown] to an L-shaped attachment member which is generally designated by the numeral 124 and best seen in FIG. 4. The attachment member 124 has a first end 125 (FIG. 3) and an opposite second end 126. The second end 126 receives a fastener 127 therethrough.

As best seen by reference to FIG. 3, the apparatus 10 of the subject invention includes a fender 140 [seen in phantom lines] and which is mounted on the attachment member 124.

The respective fenders 140 are provided to prevent debris produced during welding operations from impacting against the apparatus 10 as it operates. Referring now to FIGS. 4 and 5, the apparatus 10 includes a frame member which is generally indicated by the numeral 150, and which is secured to the attachment member 124 and more specifically the second end thereof 126, by the fastener 127. Frame member 150 has a main body 151, with opposite first and second ends 152 and 153 respectively. Still further, as seen in the exploded view of FIG. 5, a plurality of threaded apertures 154 are formed in the main body 151, and the opposite ends 152 and 153, respectively. As seen in FIG. 5, the main body 151 has a given length dimension. As seen in FIG. 3, an air knife, which is generally designated by the numeral 160, is mounted on the first end 152 of the frame member 150. The air knife 160 has an air delivery hose 161 attached thereto and which delivers a source of compressed air [not shown] to the air knife 160. A bracket 162 secures air knife 160 to frame member 150 by suitable fasteners that engage the threaded apertures 154 formed in the first end 152. The air knife 160 is operable to remove debris in front of the apparatus 10 as it moves along during welding operations.

As best seen by reference to FIG. 5, a first wheel support member or plate 170 is shown and has a main body 171. The main body 171 has an upper or first portion 172, and a lower or second portion 173. Still further the main body 171 has an inside facing surface 177, and an outside facing surface 175. A wheel receiving station 176 is formed in the inside facing surface 174. Fastener apertures 177 are formed in the upper and lower portions 172 and 173 thereof. Still further, a pair of apertures 178 are formed in the wheel receiving station 176. This structure will be discussed in greater detail hereinafter.

The apparatus 10 has a second wheel support member or plate which is generally indicated by the numeral 180 and which is located in substantially parallel spaced relation relative to the first wheel support member 170. The second wheel support plate has a main body 181, with an upper portion 182, and a second or lower portion 183. The second wheel support member or plate 180 has a substantially similar shape to that of the first wheel support plate 170. Still further, the second wheel support plate 180 has an inside facing surface 184, and an outside facing surface 185. As seen best in FIG. 5, a receiving slot 190 is formed in the upper portion 182. Still further, fastener apertures 192 are formed in the lower portion 183. Moreover, guide apertures 193 are formed in the upper portion 182. As best seen by reference to FIG. 9, a wheel receiving station 194 is formed in the inside facing surface 184 and is similar to that illustrated with respect to the first wheel support member or plate 170. Additionally, an aperture 186 is formed in the second wheel support plate 180. A location sensor 191 is borne on the outside facing surface 185. The functional relationship of this location sensor to the apparatus 10 will be discussed hereinafter. The inside facing surfaces 174 and 184 of the respective first and second wheel support plates or members of 170 and 180 respectively define a space 195 (FIG. 9).

As best seen by references to FIGS. 5, 6, and 7, the apparatus 10 of the subject invention includes a pair of propulsion assemblies or components which are generally indicated by the numeral 200. The propulsion assemblies 200 are individually operable to urge an ultrasonic signal generator and/or signal receiver along their respective paths of travel. This feature will be discussed hereinafter. The propulsion assembly 200 seen in the exploded view of FIG.

5 and in FIGS. 6 and 7 has a motor support member which is generally designated by the numeral 201. The motor support member has a main body 202, with opposite first and second ends 203 and 204 respectively. Still further, the main body has top and bottom surfaces 205 and 210 respectively. The bottom surface defines a cavity generally indicated by the numeral 211. A motor 212 is mounted on the top surface 205, and an encoder 213 is mechanically coupled to the motor. The motor 212 and encoder 213 are further electrically coupled with a programmable controller which will be discussed hereinafter. The motor 212 has a drive shaft 214 (FIG. 6) which extends through the top surface 205, and which is attached to a crank that is generally designated by the numeral 215. It should be understood, that as the motor 212 is energized, the drive shaft 214 is operable to cause the crank 215 to rotate in a plane which is substantially parallel to the top surface 205. As best seen by reference to FIG. 6, a connecting rod 220 is generally shown, and has a first end 221, which is rotatably coupled in force receiving relation relative to the crank 215. Still further, the connecting rod has a second or opposite end 222, and further has a main body 223 which extends through the receiving slot 190 (FIG. 5).

As best seen by reference to FIGS. 5 and 6, the apparatus 10 includes a drive member generally indicated by the numeral 230. The drive member 230 is slidably borne by at least one of the wheel support members, here shown as the second wheel support member 180. Still further, the drive member 230 is forcibly engaged by the connecting rod 220 and further disposed in force transmitting relation relative to the ultrasonic signal generator or receiver which will be discussed hereinafter. The drive member 230 has a main body 231 (FIG. 5) which includes an upper portion 232, and a lower portion 233. The main body 231 has a receiving station 234 formed therein which is operable to receive the second end 222 of the connecting rod 220. As seen in the exploded view of FIG. 5, a pin 235 pivotally secures the second end 222 in the receiving station 234. A pair of guide members 240 are individually received in each of the apertures 241 which are formed in the upper portion 232 thereof. Still further, an aperture 242 is formed in the lower portion 233. As best illustrated by reference to FIG. 6, the drive member 230 is moveable along a reciprocal path of travel generally indicated by the numeral 243. The path of travel 243 is defined between a first position 244, whereby the drive member 230 is disposed in juxtaposed relation relative to the second wheel support member 180, and a second position 245 whereby the drive member 230 is disposed in spaced relation relative thereto. This is illustrated most clearly by reference to FIG. 6.

Figure 8B:
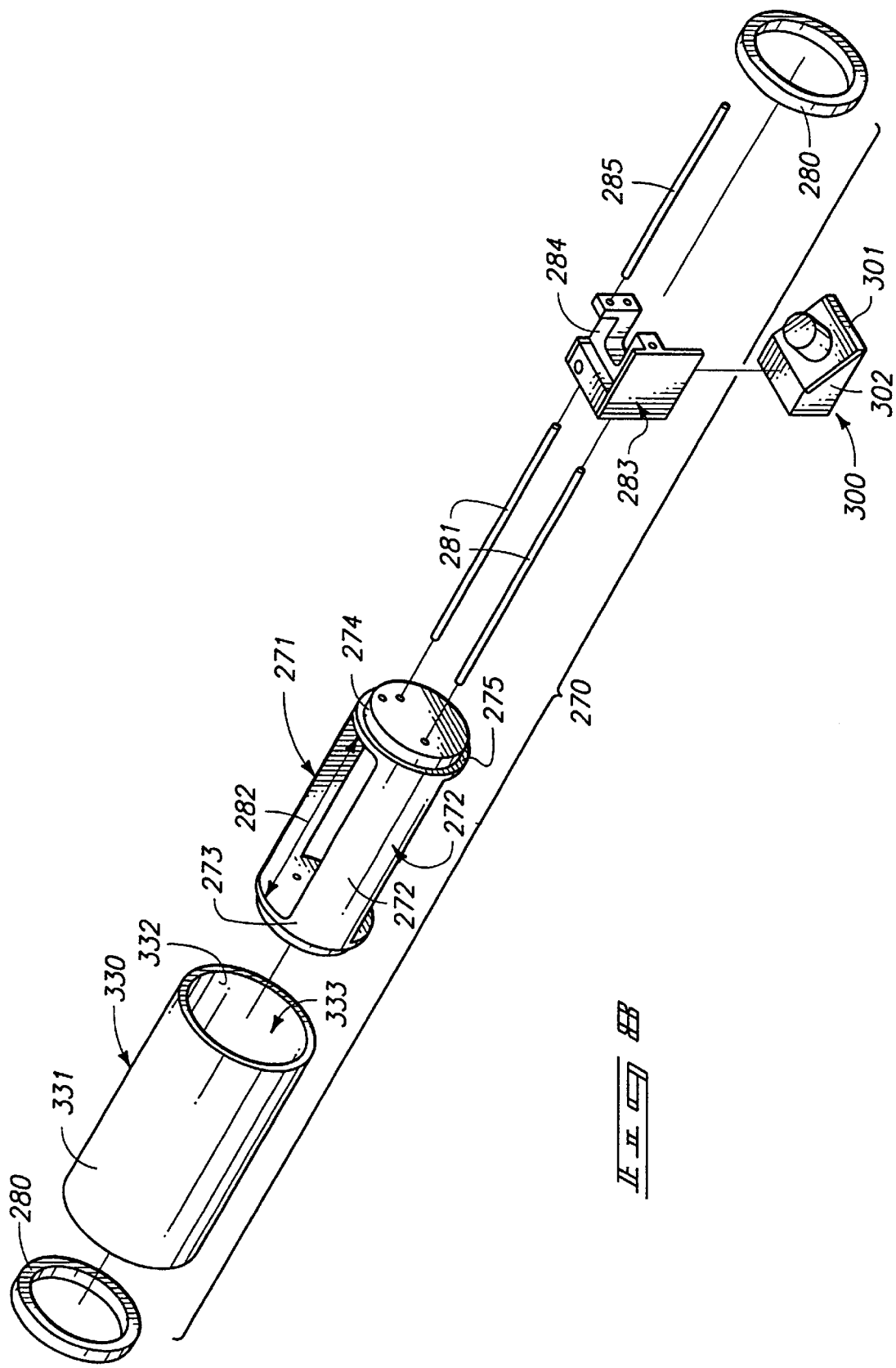
FIG. 8 is a partial, exploded, perspective view of a sensor wheel assembly which is employed with the present invention.

As best seen to reference to the exploded view of FIGS. 5 and 8, a hollow sensor wheel assembly 270 is shown and which is received in the space 195 defined between the first and second wheel support plates or members 170 and 180 respectively. The hollow sensor wheel assembly 270 includes a carriage generally designated by the numeral 271 (FIG. 8). The carriage 271 has a main body generally designated by the numeral 272 and which has opposite first, and second ends 273 and 274. Formed in the first and second ends 273 and 274 are bearing receiving stations 275. As seen in the exploded view of FIGS. 8 and 9, a bearing 280 is received in each of the bearing receiving stations 275. Still further, and extending between the first and second ends 273 and 274 are fixed guide members 281. The guide members 281 define a path of travel 282 between first and second ends 273 and 274. The guide members 281 extend beyond the carriage 271 and are received in the apertures 178 formed in the wheel receiving station 176. This arrangement fixes the position of the carriage 271 relative to the wheel support members 170 and 180. A sensor support member 283 is reciprocally slidably mounted on the guide members 281 and is operable to travel along the path of travel 282. The sensor support member 283 has a main body 284 which has affixed thereto a carriage driving rod 285. The carriage driving rod 285 exits through the aperture 186 which is formed in the second wheel support plate 180. The carriage driving rod 285 further is attached to the lower portion 233 of the drive member 230 by way of the aperture 242. As should be understood, when the motor 212 is energized, and imparts rotational movement to the crank 215, the corresponding motion of the connecting rod of 220 causes the drive member 230 to move reciprocally along the path of travel 243. This motion along the path of travel 243 causes force to be imparted along the carriage driving rod 285. This motion, in turn, causes the sensor support member 283 to reciprocally move along the path of travel 282. An ultrasonic generator or receiver and which is generally designated by the numeral 300 is borne by the carriage 271 and is operable for movement along the path of travel 282. The ultrasonic generator or receiver 300 is mounted on the sensor support member 283 and is then affixed by way of a bracket 301 to an underlying ultrasonic wedge 302 which is best seen in FIGS. 10–13 respectively. The ultrasonic wedge 302 has a main body 303 having a top surface 304. The top surface 304 is defined by a first plane 305, and a second plane 306. Still further, the main body 303 has a bottom surface 310 and sidewalls 311. As best seen in the drawings, the ultrasonic wedge 302 has a first material or portion 312 which is embedded in a second material or portion 313. The first and second portions 312 and 313 are fabricated from materials having different acoustic properties. Still further, the first material forming the first portion 312 is embedded at a predetermined angle in the second material 313. In the present invention, the first material 312 transmits or receives an ultrasonic signal 320 which is generated by the ultrasonic signal generator or receiver 300. As seen in FIG. 13, the first material 312 receives the ultrasonic signal 320 which travels along an incident angle 314 and which remains substantially constant with increasing temperature. It should be understood that the second plane 306 is positioned at a given angle to form a resulting incident angle 314 which is unique to the material forming the supporting surface 13. This incident angle 314 is chosen using standard ultrasonic methods. The first material forming the first portion 312 is selected to have the following acoustic properties: [1] the sound varies minimally as a function of temperature; [2] the ultrasonic attenuation is minimal in relative comparison to the second material forming the second portion 313; and [3] the acoustic impedance substantially matches the second material 313. An exemplary first material 312 will exhibit attenuation of about 6 dB/cm at room temperature and increases to about 9 dB/cm at 100 degrees C. An exemplary first material 312 includes a polyimide. This material can be commercially secured under the trademark MELDIN 2001. The second material 313 comprising the second portion is an Epoxide. This may be purchased from a number of different commercial sources.

In the preferred embodiment, discussed above exemplary speeds of the ultrasonic signals 320 in the first material 312 range from about 2400 m/s to about 2800 m/s. Further, exemplary speeds of the ultrasonic signal 320 generated by the ultrasonic generator 300 traveling in the second material 313 forming the second portion are also about 2400 m/s to about 2800 m/s. The ultrasonic attenuation in the first material forming the first portion 312 is about 3.0 dB/cm to about 3.5 dB/cm, and in the second material 313 the attenuation is about 8.0 dB/cm to about 9.0 dB/cm. Acoustic impedance in the first material 312 is about $3.67 \times 10^6$ kg/m$^2$s to about $3.74 \times 10^6$. Still further, in the second material 313 the acoustic impedance is about $3.00 \times 10^6$ kg/m$^2$s to about $3.15 \times 10^6$ kg/m$^2$s. In this arrangement, the speed of an ultrasonic signal 320 generated by the ultrasonic generator 300 traveling in the first material 312 varies to only a small degree as a function of increasing temperature. Still further, the ultrasonic attenuation of the second material 313 is large in relative comparison to the ultrasonic attenuation in the first material 312. The first material 312 has an ultrasonic attenuation of about 3 dB/cm at about 70 degrees F. and increases to about 3.5 dB/cm at about a temperature of about 212 degrees F. This arrangement of materials in the ultrasonic wedge 302 substantially eliminates extraneous ultrasonic signals 320 from being received by the ultrasonic receiver 300. Still further, the matching of the impedances of the first and second materials 312 and 313 ensures that any ultrasonic signals 320 traveling in the first material 312 will be transmitted into the second material 313 without any reflection of the ultrasonic signal 320 back into the first material 312. This arrangement of materials in the ultrasonic wedge 302 also ensures that the incident angle 314 remain substantially constant with the increasing temperature. An exemplary ultrasonic signal generator or receiver 300 comprises a transducer. In the preferred form of the invention the transducer comprises a piezoelectric transducer.

A hollow sensor wheel or having a tire 330 fabricated from a flexible polymeric substrate is provided, and which rotates about the carriage 271. The rotatable wheel is fabricated from a material which facilitates the transmission of ultrasonic energy and further can withstand the temperatures, and other environmental conditions which will be normally experienced during welding operations. This material is referably the same material as the first material 312 used in the ultrasonic wedge 302. Exemplary tire 330 compositions comprise natural rubber, synthetic rubber and vulcanizable elastomer. The rotatable wheel tire assembly 330 has an outside surface 331, an inside surface 332, and a cavity 333 which is defined by the inside surface 332. The bearings 280 are received in the cavity 333 and mounted endwardly of the tire 330. In this arrangement, the sensor wheel and tire assembly 330 encloses the ultrasonic generator or receiver 300 as it moves along its path of travel 282. The cavity 333 is filled with oil to provide ultrasonic signal coupling between the wedge and the wheel.

Figure 14:
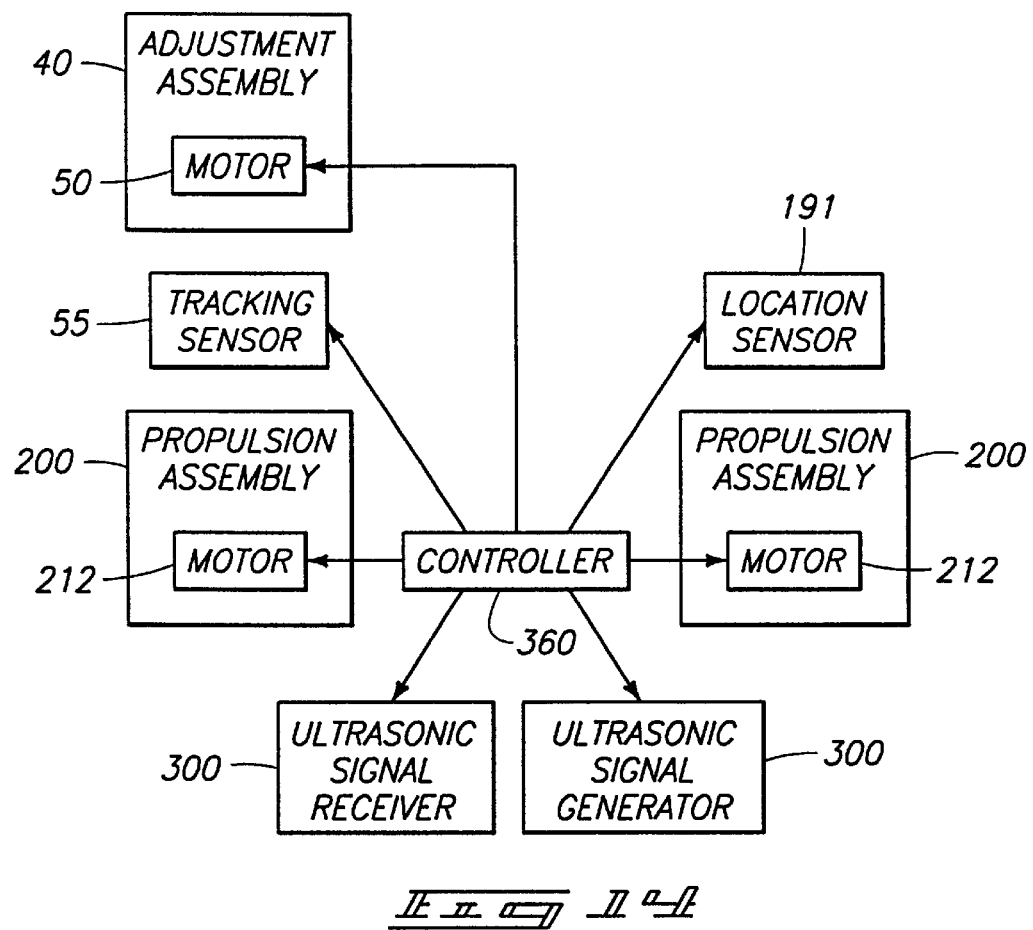
FIG. 14 is a greatly simplified schematic diagram showing the controller of the present invention.

Referring now to FIG. 14, a controller 360 is electrically coupled with the ultrasonic signal generator or receiver 300, the motor 212 of the propulsion assembly 200, the tracking sensor 55, the location sensor 191, and motor 50 of the adjustment assembly 40. The controller 360 controls the timing of the electrical impulses for each component and further controls the overall performance of the apparatus 10.

It should be understood that an ultrasonic signal generator or receiver 300 could move along the path of travel 282 by several suitable mechanisms, such as, for example, a flexible cable, a rigid rod, a lead screw, or a ball reverser.

Figure 15:
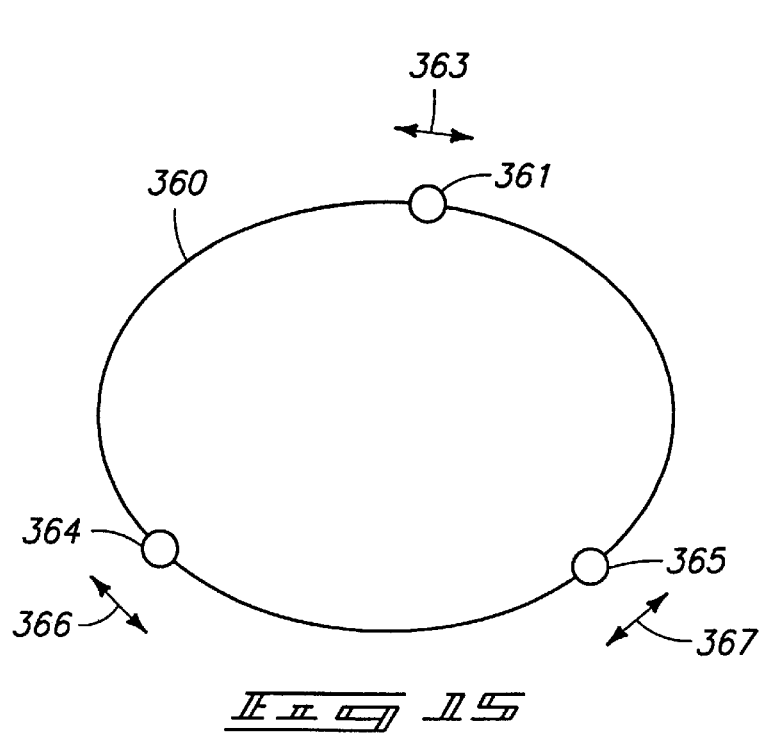
FIG. 15 is a greatly simplified schematic view of a second form of a drive member employed with the present invention.

Referring now to FIG. 15, a continuous flexible cable 360 is illustrated. Point one 361 on cable 360 is driven in an oscillating manner in a direction 363 tangential to the cable 360. Correspondingly, points two and three, 364 and 365, respectively, will also move in similar directions 366 and 367 which is tangential to the cable 360. Thus, as point one 361 is driven a distance to the right, points two 364, and point three 365, will move the same distance to the left, and vice versa. By this means, two ultrasonic signal generators or receivers 300 at points two 364, and three 365, could scan synchronously by a single drive mechanism at point one 361.

Figure 16:
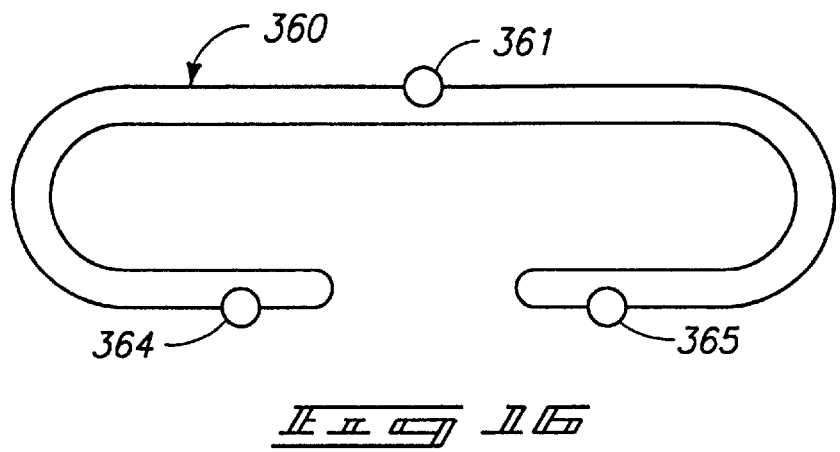
FIG. 16 is a greatly simplified schematic view of a third form of a drive member employed with the present invention.
Figure 17:
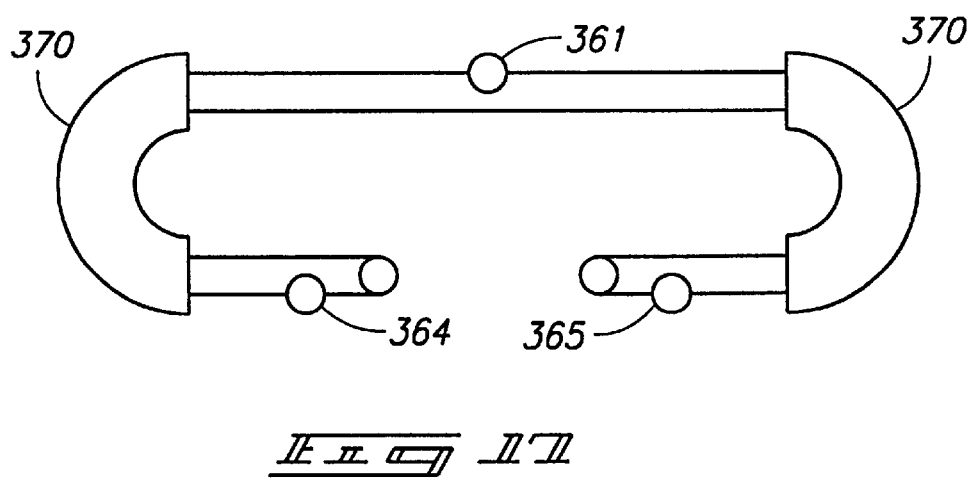
FIG. 17 is a greatly simplified schematic view of a fourth form of a drive member employed with the present invention.

FIG. 16 illustrates the same cable 360 constrained to a different path. Assuming such constraint, motion of point one 361 will produce a corresponding motion of points two 364, and three 365, in the same manner as discussed for FIG. 15 above. The path of the cable 360 can be constrained by a pair of pulleys, and/or rigid or flexible conduits 370, as shown in FIG. 17. Using this method, the amplitude of motion at points 364 and 365 is substantially equal to the amplitude of motion at point one 361. By this means, two ultrasonic signal generators or receivers 300 at points two 364, and three 365, could scan synchronously by a single drive mechanism at point one 361.

Figure 18:
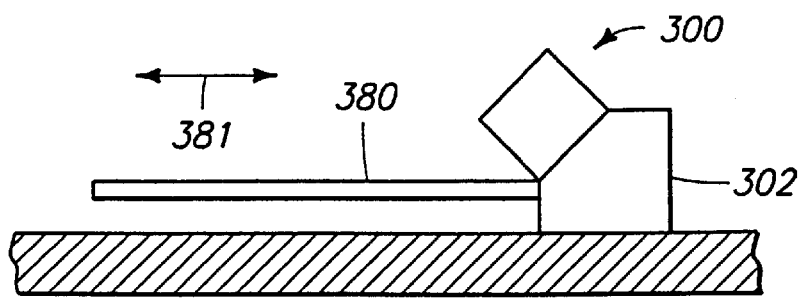
FIG. 18 is a side elevational view of a fifth form of a drive member employed with the present invention.

Another means for the synchronous movement of an ultrasonic signal generator or receiver 300 is by means of a rigid rod 380, as shown in FIG. 18. The rigid rod 380 could be attached to the ultrasonic signal generator or receiver 300 and wedge 302. The longitudinal axis of rod 380 is substantially parallel to the desired direction 381. Motion of the rod 380 then results in a corresponding motion 381 of the ultrasonic signal generator or receiver 300 and wedge 302 with the same amplitude and in the desired direction 381. By this means, a drive mechanism (not shown) could simultaneously drive the ultrasonic signal generator or receiver 300 and wedge 302. Two ultrasonic signal generators or receivers 300 and wedges 302 could scan synchronously by either a single drive mechanism, or by two drive mechanisms that are operated synchronously.

Another method for synchronized movement of the ultrasonic signal generator or receiver 300 and wedge 302 is by a lead screw (not shown) which may be located such that the center line axis of the screw is substantial parallel to the desired motion of the ultrasonic signal generator or receiver and wedge. In this arrangement the ultrasonic signal generator or receiver and wedge may be secured to a nut which is free to travel along the screw as the screw is rotated. Oscillatory rotation of the lead screw will then result in oscillatory rotation of the ultrasonic signal generator or receiver and wedge. By this means, a ultrasonic signal generator or receiver and wedge could move by either a single motor or by two motors operated synchronously.

Another method for the synchronous movement of the ultrasonic signal generator or receiver and wedge is by a ball reverser (not shown) which is a specially manufactured screw and nut assembly that produces oscillatory motion of the nut on the screw when the screw is rotated. In a manner similar to that of the lead screw, a ball reverser (not shown) may be located such that the center line axis of the screw is parallel to the desired direction of motion of the ultrasonic signal generator or receiver and wedge. The ultrasonic signal generator or receiver and wedge may be secured to the nut assembly and is free to travel on the screw as the screw is rotated. Rotation of the ball reverser will then result in oscillatory motion of the ultrasonic signal generator or receiver and wedge. Either a single or plurality of motors could operate synchronously to rotate the screw.

Motor Synchronization

In order for the ultrasonic signal generator or receiver 300 (hereinafter referred to as transducer) to properly inspect the partially completed weld 15, the transducer 300 must take ultrasonic data at specific predetermined locations during a scan. A location of the transducer at the time of a scan must be known within approximately one millimeter. In addition, the two transducers operate independently; however, to achieve accurate ultrasonic data, the relative position of the two transducers 300 must also be kept within approximately one millimeter.

Figure 20:
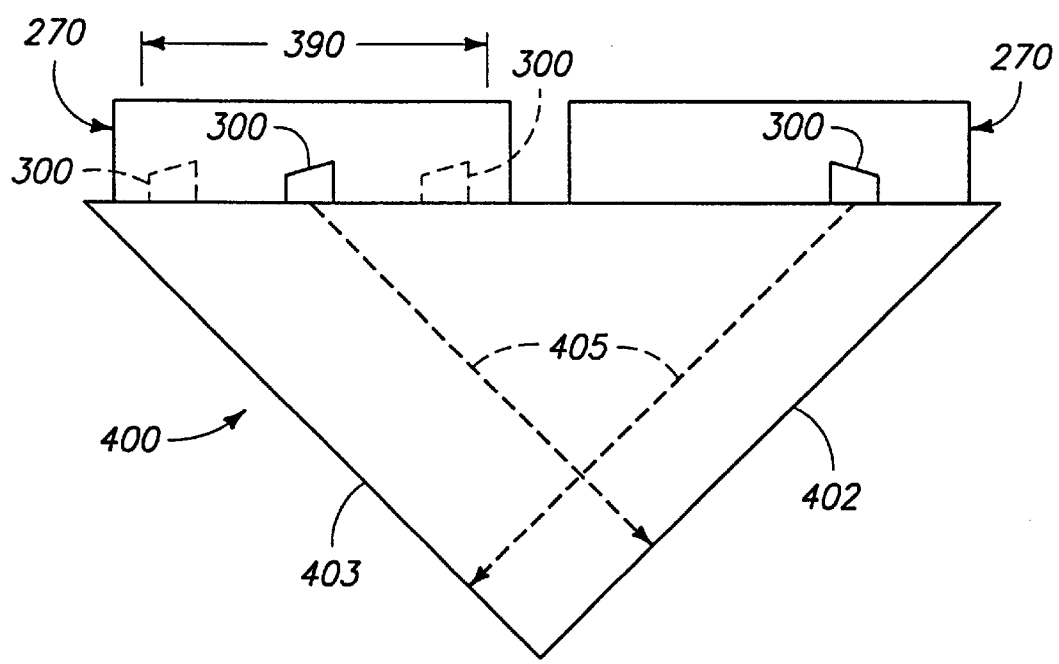
FIG. 20 is a simplified schematic view of the inspection apparatus and calibration block of FIG. 19.

The transducers 300 are moved, as noted above by the two separate motors 212. As stated previously, the respective motors 212 move the drive member 230 and the respective transducers 300 which are attached thereto. As should be understood, one revolution of the drive shaft 214, and the crank 215 corresponds to one complete cycle of the transducer 300 along path of travel 282. The location sensor 191 mounted on the second wheel support plate 180 switches a voltage signal when the position of the drive member 230 corresponds to the transducer 300 being near one end of its range of motion or travel. The exact end of motion of the transducers 300 is called "Top Dead Center" or TDC 390 (FIG. 20). This information is coordinated with the encoders 213, described above. Exemplary encoders 213 comprise relative optical encoders. Since the encoders 213 are relative devices, when the controller 360 is turned on, the actual rotational position of the drive shaft 214 is unknown, and correspondingly, the actual positions of the transducers 300 and wedges 302 in the hollow sensor wheel assembly 270 are unknown. Consequently, in order to obtain an absolute transducer 300 and wedge 302 position, the encoders 213 must be calibrated so each indicates an exact integer of revolutions when the transducers 300 are at the absolute TDC 390.

Figure 19:
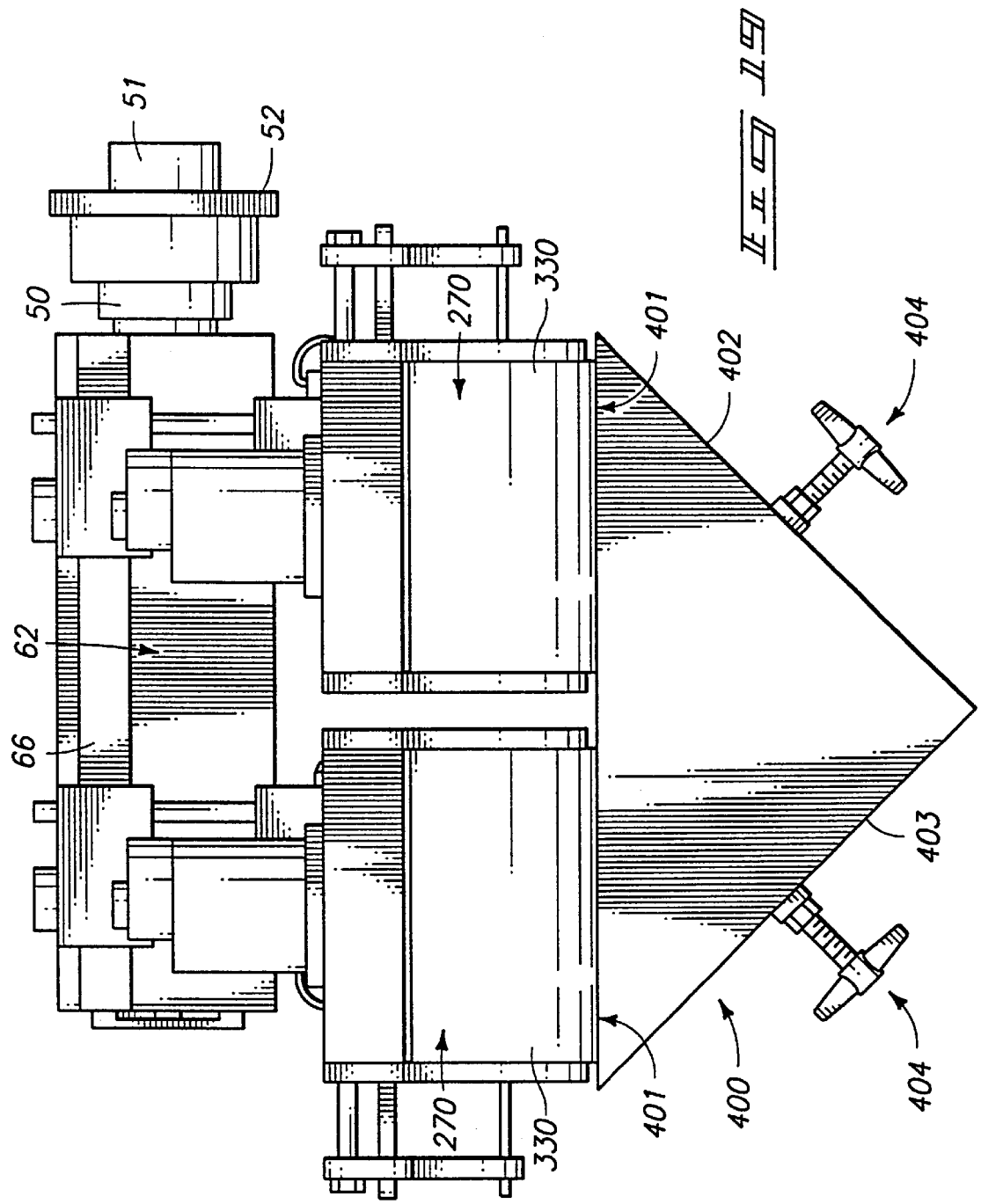
FIG. 19 is an elevational view of the inspection apparatus in combination with a calibration block and which is employed with same.

This calibration is performed in two parts: (1) The difference in the position of transducer 300 when the location sensor 191 signals (near the absolute TDC position 390) and the absolute TDC 390 position is determined by an ultrasonic measurement using a calibration block 400 described hereinafter (FIG. 19). This difference is called the sensor-TDC offset value. (2) Before each acquisition of data from the partially completed weld 15, the respective transducers 300 are both moved to absolute TDC 390 position by first moving them to the position where the location sensor 191 switches, and then by moving the extra distance (the sensor-TDC offset) determined in step 1 to TDC 390, described hereinafter. Then, during data acquisition, the motors 212 are synchronized on each cycle by insuring the encoder 213 readings track each other during the motion by using the same integers for the same locations, relative one to another, within the hollow sensor wheel assembly 270.

Transducer Position Calibration

Referring now to FIGS. 19–20, the hollow sensor wheel assembly 270 is mounted on a calibration block 400 with the wheel and tire assemblies 330 resting on an upper edge or surface 401. The calibration block is fabricated as a triangle with two opposing edges or surfaces 402 and 403 oriented at about 45 degrees to the upper edge surface 401. The calibration block 400 comprises steel plates which may be adjusted by an adjustment mechanism 404.

By scanning the transducer 300 (FIG. 20), it is possible to measure the distances from the transducers 300 to each of the two opposing edge surfaces 402 and 403. Each transducer 300 is stepped through a full rotation in about 20 increments. At each increment, the time of the reflected beam 405 is used to record the distance from the transducers 300 to the opposed edge surfaces 402 and 403, and correspondingly, the encoder 213 is queried for its position. A resulting sinusoidal curve is fitted to the measurements, and from that information the relation of the transducer 300 to the encoder 213 is determined. The resulting signals are recorded as approximate sine waves. The maximum and minimum of the sine waves correspond to the extreme TDC 390 positions of the respective transducers 300. By correlating these positions to the corresponding relative encoder values (integers), it is possible to correct the encoders such that they register the absolute TDC 390, hereinafter more thoroughly discussed (at least until the controller 360 is turned off).

In order to avoid having to run this calibration process every time the controller 360 is turned on, a second calibration step is used. The location sensor 191 detects a position of the drive member 230 that is near, but not, as stated previously, the absolute TDC location 390 of the transducer 300. However, by comparing the encoder value (integer) at which the location sensor 191 activates, and the encoder value corresponding to the absolute TDC 390 location found in the previous calibration step, the sensor-TDC offset value and the location of the absolute TDC 390 may be obtained. This sensor-TDC offset value does not change unless the hollow sensor wheel assembly 270 is taken apart and/or reassembled. Consequently, the next time a controller 370 is turned on, the motor 212 is used to move the drive member 230 to the location at which the location sensor 191 activates. Then the sensor TDC offset is added to the encoder value to convert it to an absolute value.

IN OPERATION

The operation of the described embodiment of the present invention is believed to be readily apparent and is briefly summarized at this point.

The apparatus 10 for the concurrent inspection of partially completed welds 15 includes a moveable welder 20 for forming a partially completed weld 15 between two adjoining supporting surfaces 13 or metal substrates and wherein the partially completed weld 15 has opposite sides 14. An ultrasonic signal generator 300 is mounted on the moveable welder 20 and generates an ultrasonic signal 320 which is directed toward one side 14 of the partially completed weld 15. The ultrasonic signal generator 300 is reciprocally moveable along a path of travel 282 which is substantially normal to the side of the partially completed weld 15 and laterally outwardly relative thereto.

In the present invention 10, an ultrasonic signal receiver 300 is mounted on the moveable welder 20 and receives the ultrasonic signal 320 emitted by the ultrasonic signal generator 300 and which are reflected or diffracted from one side of the partially completed weld 15, or which pass through a given region of the partially completed weld 15. The ultrasonic signal generator or receiver 300 is reciprocally moveable along a path of travel 282 which is substantially normal to the side of the partially completed weld 15, and laterally outwardly relative thereto. The movement of the ultrasonic signal receiver 300 is coordinated with the ultrasonic signal generator 300 on the opposite side of the partially completed weld. Further, the relative locations of the paths of travel 282 may be adjusted by way of the adjustment assembly 40.

A pair of propulsion assemblies 200 are individually operable to urge the ultrasonic signal generator and/or receiver 300 along its respective paths of travel 282. Each propulsion assembly 200 has a motor support member 201 which is movably borne on the moveable welder 20. A motor 212 is borne on the motor support member 201 and has a drive shaft 214. A crank 215 is borne on the drive shaft 214 and is rotatable therewith. A pair of wheel support members 170 and 180 respectively are mounted on the motor support member 201 and depend downwardly therefrom. The wheel support members 170 and 180 define a space 195 therebetween which receives a carriage 271. The carriage supports and carries the ultrasonic signal generator or receiver 300 along their respective path of travel 282. A connecting rod 220 is rotatably mounted on the crank 215, and a drive member 230 is slidably borne by at least one of the wheel support members 170 and 180. The connecting rod forcibly engages the drive member 230, and further is disposed in force transmitting relation relative to the ultrasonic signal generator or receiver 300. The motor 212, when energized, causes the ultrasonic signal generator or receiver 300 to reciprocally move along the path of travel 282 which is defined by the carriage 271.

A hollow sensor wheel assembly 270 is received in the space 195 defined between the wheel support members 170 and 180 and is supported therebetween. The sensor wheel assembly 270 has a wheel and tire assembly 330 which defines an internal cavity 333 which receives the ultrasonic sensor or receiver 300 and the associated carriage 271 and which encloses the path of travel 282 of the ultrasonic signal generator or receiver 300. The hollow sensor wheel and tire assembly 330 is received in each of the wheel receiving stations 176 and 194 and rotates about the ultrasonic signal generator or receiver 300 by means of the bearing 280.

An adjustment assembly 40 is borne by the moveable welder 20 and attached to the motor support member 201 of each propulsion assembly 200. The adjustment assembly 40 selectively alters the position of each path of travel 282 of the ultrasonic signal generator or receiver 300 relative to the opposite sides 14 of the partially completed weld 15. The adjustment assembly 40 comprises a guide member 41, and a motor 50 is borne by the guide member 41. This second motor 50 is electrically coupled with the controller 360. A second drive member 45 is coupled with the second motor 50 and disposed in force transmitting relation relative to the respective motor support members 201.

A location sensor 191 is borne by the propulsion assembly 200 and determines the location of the ultrasonic sensor or receiver 300 as it moves along the respective paths of travel 242.

A tracking sensor 55 is borne by the adjustment assembly 40 and locates the partially completed weld 15. The tracking sensor 55 ensures the proper orientation of the respective ultrasonic signal generator or receiver 300 relative to the opposite sides 14 of the partially completed weld 15.

An ultrasonic wedge 302 is provided for transmitting or receiving the ultrasonic signal 302 which is generated or received from the ultrasonic signal generator 300. The ultrasonic wedge 302 is slidably borne by the carriage 271 and moves in unison with ultrasonic signal generator or receiver along the path travel 282. The ultrasonic wedge 302 is formed of first and second materials 312 and 313 having different acoustic properties, and wherein the first material 312 is imbedded at a predetermined angle in the second material 313. The first material 312 transmits or receives the ultrasonic signal 320 which is generated by the ultrasonic signal generator 300, and the first material 312 receives the ultrasonic signal 320 which travels along an incident angle 314 which remains substantially constant with increasing temperature.

A controller 360 is electrically coupled with the ultrasonic signal generator and/or receiver 300 and initiates the generation of ultrasonic signals 320 and processes the ultrasonic signal 320 received by the ultrasonic signal receiver 300 while each propulsion assembly 200 coordinates the movement of the ultrasonic signal generator and/or receiver 300 relative to the opposite sides 14 of the partially completed weld 15.

In compliance with the statute, the invention has been described in language more or less specific as to structural and methodical features. It is to be understood, however, that the invention is not limited to the specific features shown and described, since the means herein disclosed comprise preferred forms of putting the invention into effect. The invention is, therefore, claimed in any of its forms or modifications within the proper scope of the appended claims appropriately interpreted in accordance with the doctrine of equivalents.

We claim:

1. An apparatus for the concurrent inspection of partially completed welds, comprising:

a moveable welder for forming a partially completed weld;

an ultrasonic generator mounted on the moveable welder and which is reciprocally moveable along a path of travel which is laterally disposed relative to the partially completed weld; and an ultrasonic wedge oriented in ultrasonic signal receiving relation relative to the ultrasonic generator, and wherein the ultrasonic wedge comprises first and second materials, and wherein the speed of an ultrasonic signal generated by the ultrasonic generator traveling in the first material varies to only a small degree as a function of increasing temperature, and wherein the second material has an ultrasonic attenuation which is large in relative comparison to the ultrasonic attenuation in the first material.

2. An apparatus for the concurrent inspection of partially completed welds, comprising:

a moveable welder for forming a partially completed weld;

an ultrasonic generator mounted on the moveable welder and which is reciprocally moveable along a path of travel which is laterally disposed relative to the partially completed weld; and an ultrasonic wedge oriented in ultrasonic signal receiving relation relative to the ultrasonic generator, and wherein the ultrasonic wedge comprises first and second materials each having an ultrasonic impedance and attenuation, and wherein the speed of an ultrasonic signal generated by the ultrasonic generator traveling in the first material varies to only a small degree as a function of increasing temperature, the ultrasonic attenuation is as small as possible, and the acoustic impedance is substantially similar to that of the second material, and wherein the second material has an ultrasonic attenuation which is large in relative comparison to the ultrasonic attenuation in the first material.

3. An apparatus for the concurrent inspection of partially completed welds, comprising:

a moveable welder for forming a partially completed weld;

an ultrasonic generator mounted on the moveable welder and which is reciprocally moveable along a path of travel which is laterally disposed relative to the partially completed weld; and an ultrasonic wedge disposed in ultrasonic signal receiving relation relative to the ultrasonic generator, and wherein the ultrasonic wedge transmits ultrasonic signals along an incident angle to an underlying metal substrate which is being concurrently welded by the moveable welder, and wherein the ultrasonic signal traveling through the ultrasonic wedge enters the metal substrate and travels along a refracted angle, and wherein the ultrasonic signal has a speed of travel in the ultrasonic wedge which changes with an increase in temperature in a manner such that the angle of incidence remains substantially constant and independent of temperature.

4. An apparatus for the concurrent inspection of partially completed welds, comprising:
   a moveable welder for forming a partially completed weld;
   an ultrasonic generator mounted on the moveable welder and which is reciprocally moveable along a path of travel which is laterally disposed relative to the partially completed weld; and
   an ultrasonic wedge oriented in ultrasonic signal receiving relation relative to the ultrasonic generator, and wherein the ultrasonic wedge comprises first and second materials, and wherein the speed of an ultrasonic signal generated by the ultrasonic generator traveling in the first material varies to only a small degree as a function of increasing temperature, and wherein the second material has an ultrasonic attenuation which is large in relative comparison to the ultrasonic attenuation in the first material, and wherein the first material has an ultrasonic attenuation of about 3 dB/cm at about 70 degrees F., and increases to about 3.5 dB/cm at a temperature of about 212 degrees F.

5. An apparatus for the concurrent inspection of partially completed welds, comprising:
   a moveable welder for forming a partially completed weld;
   an ultrasonic generator mounted on the moveable welder and which is reciprocally moveable along a path of travel which is laterally disposed relative to the partially completed weld; and
   an ultrasonic wedge for receiving an ultrasonic signal generated by the ultrasonic generator, and wherein the ultrasonic wedge is formed of first and second materials having different acoustic properties, and wherein the first material is imbedded at a predetermined angle in the second material, and wherein the first material receives the ultrasonic signal which travels along an incident angle which remains substantially constant with increasing temperature.

6. An apparatus for the concurrent inspection of partially completed welds, comprising:
   a moveable welder for forming a partially completed weld;
   an ultrasonic generator mounted on the moveable welder and which is reciprocally moveable along a path of travel which is laterally disposed relative to the partially completed weld; and
   an ultrasonic wedge for receiving an ultrasonic signal generated by the ultrasonic generator, and wherein the ultrasonic wedge is formed of first and second materials having different acoustic properties, and wherein the first material is a polyimide which is imbedded at a predetermined angle in the second material, and wherein the first polyimide material receives the ultrasonic signal which travels along an incident angle which remains substantially constant with increasing temperature, and the second material has an ultrasonic attenuation which is large in relative comparison to the first polyimide material, and an acoustic impedance which is substantially similar to that of the first polyimide material.

7. An apparatus for the concurrent inspection of partially completed welds, comprising:
   a moveable welder for forming a partially completed weld;
   an ultrasonic generator mounted on the moveable welder and which is reciprocally moveable along a path of travel which is laterally disposed relative to the partially completed weld;
   a propulsion assembly for reciprocally moving the ultrasonic generator along the path of travel, and wherein the propulsion assembly further comprises a motor; a crank disposed in force receiving relation relative to the motor; a connecting rod rotatably coupled to the crank; and a drive member disposed in force receiving relation relative to the connecting rod and in force transmitting relation relative to the ultrasonic generator; and wherein a carriage is provided which supports and guides the ultrasonic generator along the path of travel;
   an ultrasonic wedge disposed in ultrasonic signal receiving relation relative to the ultrasonic generator, and which moves in unison along the path of travel with the ultrasonic generator, and wherein the ultrasonic signal received by the ultrasonic wedge travels along an incident angle which is substantially unaffected by increases in temperature; and
   a hollow sensor wheel which receives and encloses the carriage and the associated ultrasonic generator and ultrasonic wedge, and wherein the hollow sensor wheel rotates about the carriage and the associated ultrasonic generator and ultrasonic wedge.

8. An apparatus for the concurrent inspection of partially completed welds, comprising:
   a moveable welder for forming a partially completed weld;
   an ultrasonic generator mounted on the moveable welder and which is reciprocally moveable along a path of travel which is laterally disposed relative to the partially completed weld;
   a propulsion assembly for reciprocally moving the ultrasonic generator along the path of travel, and wherein the propulsion assembly further comprises a motor; a crank disposed in force receiving relation relative to the motor; a connecting rod rotatably coupled to the crank; and a drive member disposed in force receiving relation relative to the connecting rod and in force transmitting relation relative to the ultrasonic generator; and wherein a carriage is provided which supports and guides the ultrasonic generator along the path of travel;
   an ultrasonic wedge disposed in ultrasonic signal receiving relation relative to the ultrasonic generator, and which moves in unison along the path of travel with the ultrasonic generator, and wherein the ultrasonic signal received by the ultrasonic wedge travels along an incident angle which is substantially unaffected by increases in temperature;
   a hollow sensor wheel which receives and encloses the carriage and the associated ultrasonic generator and ultrasonic wedge, and wherein the hollow sensor wheel rotates about the carriage and the associated ultrasonic generator and ultrasonic wedge; and
   an adjustment assembly borne by the moveable welder and operable to selectively alter the location of the path of travel by moving the hollow sensor wheel to selected location laterally outwardly relative to the partially completed weld.

9. An apparatus for the concurrent inspection of partially completed welds, comprising:
   a moveable welder for forming a partially completed weld;

an ultrasonic generator mounted on the moveable welder and which is reciprocally moveable along a path of travel which is laterally disposed relative to the partially completed weld;

a propulsion assembly for reciprocally moving the ultrasonic generator along the path of travel, and wherein the propulsion assembly further comprises a motor; a crank disposed in force receiving relation relative to the motor; a connecting rod rotatably coupled to the crank; and a drive member disposed in force receiving relation relative to the connecting rod and in force transmitting relation relative to the ultrasonic generator; and wherein a carriage is provided which supports and guides the ultrasonic generator along the path of travel;

an ultrasonic wedge disposed in ultrasonic signal receiving relation relative to the ultrasonic generator, and which moves in unison along the path of travel with the ultrasonic generator, and wherein the ultrasonic signal received by the ultrasonic wedge travels along an incident angle which is substantially unaffected by increases in temperature;

a location sensor which determines the location of the ultrasonic generator and associated ultrasonic wedge as they move along the path of travel;

a hollow sensor wheel which receives and encloses the carriage and the associated ultrasonic generator and ultrasonic wedge, and wherein the hollow sensor wheel rotates about the carriage and the associated ultrasonic generator and ultrasonic wedge; and an adjustment assembly borne by the moveable welder and operable to selectively alter the location of the path of travel by moving the hollow sensor wheel to selected location laterally outwardly relative to the partially completed weld.

10. An apparatus as claimed in claim 9, wherein the ultrasonic wedge is slidably borne by the carriage, and wherein the ultrasonic wedge is formed of first and second materials having different acoustic properties, and wherein the first material is imbedded at a predetermined angle in the second material, and wherein the first material transmits or receives the ultrasonic signal which is generated by the ultrasonic signal generator, and wherein the first material receives the ultrasonic signal which travels along an incident angle which remains substantially constant with increasing temperature.

11. An apparatus as claimed in claim 10, wherein the first and second materials each having an ultrasonic impedance and attenuation, and wherein the speed of the ultrasonic signal generated by the ultrasonic generator traveling in the first material varies to only a small degree as a function of increasing temperature, the ultrasonic attenuation is as small as possible, and the acoustic impedance is substantially similar to that of the second material, and wherein the second material has an ultrasonic attenuation which is large in relative comparison to the ultrasonic attenuation in the first material.

12. An apparatus as claimed in claim 11, in the speed of the ultrasonic signal is about 2620 m/s to about 2670 m/s in the first material; the ultrasonic attenuation in the first material is about 3.0 dB/cm to about 3.5 dB/cm, and in the second material is about 8.0 dB/cm to about 9.0 dB/cm; and wherein the acoustic impedance in the first material is about $3.67 \times 10^6$ kg/m2 s to about $3.74 \times 10^6$ kg/m2 s, and in the second material about $3.00 \times 10^6$ kg/m2s to about $3.15 \times 10^6$ kg/m2 s.

13. An apparatus as claimed in claim 12, wherein the first material comprises a polyimide, and the second material is selected from the group comprising Epoxide.

14. An apparatus for the concurrent inspection of partially completed welds, comprising:

a moveable welder for forming a partially completed weld on a substrate;

an ultrasonic generator mounted on the moveable welder and which is reciprocally moveable along a path of travel which is laterally disposed relative to the partially completed weld;

a hollow sensor wheel assembly enclosing the ultrasonic generator, the hollow sensor wheel assembly comprising a material which facilitates the transmission of an ultrasonic signal generated by the ultrasonic generator to the partially completed weld without the use of a couplant between the hollow sensor wheel assembly and substrate; and an ultrasonic wedge oriented in ultrasonic signal receiving relation relative to the ultrasonic generator, and wherein the ultrasonic wedge comprises first and second materials, and wherein the speed of an ultrasonic signal generated by the ultrasonic generator traveling in the first material varies to only a small degree as a function of increasing temperature, and wherein the second material has an ultrasonic attenuation which is large in relative comparison to the ultrasonic attenuation in the first material.

15. An apparatus as claimed in claim 14, wherein the material forming the hollow sensor wheel assembly is substantially the same as the first material of the ultrasonic wedge.

16. An apparatus as claimed in claim 14, wherein the material forming the hollow sensor wheel assembly and the first material of the ultrasonic wedge establish an acoustic medium which facilitates the ultrasonic signal movement along an incident angle which remains substantially constant and independent of temperature.

17. An apparatus for the concurrent inspection of partially completed welds, comprising:

a moveable welder for forming a partially completed weld on a substrate;

an ultrasonic generator mounted on the moveable welder and which is reciprocally moveable along a path of travel which is laterally disposed relative to the partially completed weld; and a hollow sensor wheel assembly enclosing the ultrasonic generator, the hollow sensor wheel assembly comprising a material which facilitates the transmission of an ultrasonic signal generated by the ultrasonic generator to the partially completed weld without the use of a couplant between the hollow sensor wheel assembly and substrate; and an ultrasonic wedge oriented in ultrasonic signal receiving relation relative to the ultrasonic generator, and wherein the ultrasonic wedge comprises first and second materials each having an ultrasonic impedance and attenuation, and wherein the speed of an ultrasonic signal generated by the ultrasonic generator traveling in the first material varies to only a small degree as a function of increasing temperature, the ultrasonic attenuation is as small as possible, and the acoustic impedance is substantially similar to that of the second material, and wherein the second material has an ultrasonic attenuation which is large in relative comparison to the ultrasonic attenuation in the first material.

18. An apparatus for the concurrent inspection of partially completed welds, comprising:

a moveable welder for forming a partially completed weld on a substrate;

an ultrasonic generator mounted on the moveable welder and which is reciprocally moveable along a path of travel which is laterally disposed relative to the partially completed weld; and a hollow sensor wheel assembly enclosing the ultrasonic generator, the hollow sensor wheel assembly comprising a material which facilitates the transmission of an ultrasonic signal generated by the ultrasonic generator to the partially completed weld without the use of a couplant between the hollow sensor wheel assembly and substrate; and an ultrasonic wedge disposed in ultrasonic signal receiving relation relative to the ultrasonic generator, and wherein the ultrasonic wedge transmits ultrasonic signals along an incident angle to an underlying metal substrate which is being concurrently welded by the moveable welder, and wherein the ultrasonic signal traveling through the ultrasonic wedge enters the metal substrate and travels along a refracted angle, and wherein the ultrasonic signal has a speed of travel in the ultrasonic wedge which changes with an increase in temperature in a manner such that the angle of incidence remains substantially constant and independent of temperature.

19. An apparatus for the concurrent inspection of partially completed welds, comprising:

a moveable welder for forming a partially completed weld on a substrate;

an ultrasonic generator mounted on the moveable welder and which is reciprocally moveable along a path of travel which is laterally disposed relative to the partially completed weld;

a hollow sensor wheel assembly enclosing the ultrasonic generator, the hollow sensor wheel assembly comprising a material which facilitates the transmission of an ultrasonic signal generated by the ultrasonic generator to the partially completed weld without the use of a couplant between the hollow sensor wheel assembly and substrate; and an ultrasonic wedge oriented in ultrasonic signal receiving relation relative to the ultrasonic generator, and wherein the ultrasonic wedge moves in unison with the ultrasonic generator along the path of travel, and wherein the ultrasonic wedge comprises two different materials, one material comprising a polyimide and the other material comprising an Epoxide.

20. An apparatus for the concurrent inspection of partially completed welds, comprising:

a moveable welder for forming a partially completed weld on a substrate;

an ultrasonic generator mounted on the moveable welder and which is reciprocally moveable along a path of travel which is laterally disposed relative to the partially completed weld; and a hollow sensor wheel assembly enclosing the ultrasonic generator, the hollow sensor wheel assembly comprising a material which facilitates the transmission of an ultrasonic signal generated by the ultrasonic generator to the partially completed weld without the use of a couplant between the hollow sensor wheel assembly and substrate; and an ultrasonic wedge for receiving an ultrasonic signal generated by the ultrasonic generator, and wherein the ultrasonic wedge is formed of first and second materials having different acoustic properties, and where in the first material is imbedded at a predetermined angle in the second material, and wherein the first material receives the ultrasonic signal which travels along an incident angle which remains substantially constant with increasing temperature.

21. An apparatus for the concurrent inspection of partially completed welds, comprising:

a moveable welder for forming a partially completed weld on a substrate; an ultrasonic generator mounted on the moveable welder and which is reciprocally moveable along a path of travel which is laterally disposed relative to the partially completed weld; and a hollow sensor wheel assembly enclosing the ultrasonic generator, the hollow sensor wheel assembly comprising a material which facilitates the transmission of an ultrasonic signal generated by the ultrasonic generator to the partially completed weld without the use of a couplant between the hollow sensor wheel assembly and substrate; and a propulsion assembly disposed in driving relation relative to the ultrasonic generator to reciprocally move the ultrasonic generator along the path of travel; and an ultrasonic wedge received in the sensor wheel and which receives ultrasonic signals generated by the ultrasonic generator and which travel along an incident angle which remains substantially constant with increasing temperature.

22. An apparatus for the concurrent inspection of partially completed welds, comprising:

a moveable welder for forming a partially completed weld between two adjoining metal substrates, and wherein the partially completed weld has opposite sides;

an ultrasonic signal generator mounted on the moveable welder and which generates an ultrasonic signal which is directed toward one side of the partially completed weld, and wherein the ultrasonic signal generator is reciprocally moveable along a path of travel which is substantially normal to the side of the partially completed weld and laterally outwardly relative thereto, and wherein the moveable welder moves along a path of travel and the ultrasonic generator is located in spaced trailing relation relative to the moveable welder, and further operates concurrently with the operation of the moveable welder;

an ultrasonic signal receiver mounted on the moveable welder and which receives the ultrasonic signal emitted by the ultrasonic signal generator and which are reflected or diffracted from one side of the partially completed weld or which pass through a given region of the partially completed weld, and wherein the ultrasonic signal receiver is reciprocally moveable along a path of travel which is substantially normal to the side of the partially completed weld, and laterally outwardly relative thereto, and wherein the movement of the ultrasonic signal receiver is coordinated with the ultrasonic signal generator;

a pair of propulsion assemblies which are individually operable to urge the ultrasonic signal generator and the ultrasonic signal receiver along their respective paths of travel, and wherein each propulsion assembly has a motor support member movably borne on the moveable welder; a motor borne on the motor support and having a drive shaft; a crank borne on the drive shaft and rotatable therewith; a pair of wheel support members mounted on the motor support and depending downwardly therefrom, the wheel support member defining a space therebetween; a carriage extending between the respective wheel support members and which supports and carries the ultrasonic signal generator or receiver along their respective paths of travel; a connecting rod rotatably mounted on the crank; and a drive member slidably borne by at least one of the wheel support members, forcibly engaged by the connecting rod, and further disposed in force transmitting relation relative to the ultrasonic signal generator or receiver; and wherein the motor, when energized causes the ultrasonic signal generator or receiver to reciprocally move along the path of travel which is defined by the carriage; and an ultrasonic wedge for transmitting or receiving the ultrasonic signal which is generated or received from the ultrasonic signal generator, and wherein the ultrasonic wedge is slidably borne by the carriage and moves in unison along the path travel with each of the ultrasonic signal generator or receiver, and wherein the ultrasonic wedge is formed of first and second materials having different acoustic properties, and wherein the first material is imbedded at a predetermined angle in the second material, and wherein the first material transmits or receives the ultrasonic signal which is generated by the ultrasonic signal generator, and wherein the first material receives the ultrasonic signal which travels along an incident angle which remains substantially constant with increasing temperature.

23. An apparatus for the concurrent inspection of partially completed welds, comprising:

a moveable welder for forming a partially completed weld between two adjoining metal substrates, and wherein the partially completed weld has opposite sides;

an ultrasonic signal generator mounted on the moveable welder and which generates an ultrasonic signal which is directed toward one side of the partially completed weld, and wherein the ultrasonic signal generator is reciprocally moveable along a path of travel which is substantially normal to the side of the partially completed weld and laterally outwardly relative thereto, and wherein the moveable welder moves along a path of travel and the ultrasonic generator is located in spaced trailing relation relative to the moveable welder, and further operates concurrently with the operation of the moveable welder;

an ultrasonic signal receiver mounted on the moveable welder and which receives the ultrasonic signal emitted by the ultrasonic signal generator and which are reflected or diffracted from one side of the partially completed weld or which pass through a given region of the partially completed weld, and wherein the ultrasonic signal receiver is reciprocally moveable along a path of travel which is substantially normal to the side of the partially completed weld, and laterally outwardly relative thereto, and wherein the movement of the ultrasonic signal receiver is coordinated with the ultrasonic signal generator;

a pair of propulsion assemblies which are individually operable to urge the ultrasonic signal generator and the ultrasonic signal receiver along their respective paths of travel, and wherein each propulsion assembly has a motor support member movably borne on the moveable welder; a motor borne on the motor support and having a drive shaft; a crank borne on the drive shaft and rotatable therewith; a pair of wheel support members mounted on the motor support and depending downwardly therefrom, the wheel support member defining a space therebetween; a carriage extending between the respective wheel support members and which supports and carries the ultrasonic signal generator or receiver along their respective paths of travel; a connecting rod rotatably mounted on the crank; and a drive member slidably borne by at least one of the wheel support members, forcibly engaged by the connecting rod, and further disposed in force transmitting relation relative to the ultrasonic signal generator or receiver; and wherein the motor, when energized causes the ultrasonic signal generator or receiver to reciprocally move along the path of travel which is defined by the carriage;

a hollow sensor wheel received in the space defined between the wheel support members and rotatably supported thereby, and wherein sensor wheel defines an internal cavity which receives the ultrasonic sensor or receiver and the associated carriage which defines the path of travel for the ultrasonic signal generator or receiver, and wherein hollow sensor wheel rotates about the ultrasonic signal generator or receiver;

an adjustment assembly borne by the moveable welder and mounted on the motor support member of each propulsion assembly, and wherein the adjustment assembly selectively alters the position of each path of travel of the ultrasonic signal generator or receiver relative to the opposite sides of the partially completed weld, and wherein the adjustment assembly comprises a guide member; a second motor borne by the guide member and electrically coupled with the controller, and a second drive member coupled with the second motor and disposed in force transmitting relation relative to the respective motor support members;

a location sensor borne by the propulsion assembly and which determines the location of the ultrasonic sensor or receiver as it moves along the respective paths of travel;

a tracking sensor borne by the adjustment assembly and locating the partially completed weld, the tracking sensor facilitating the proper orientation of the respective ultrasonic signal generator or receiver relative to the opposite sides of the partially completed weld;

an ultrasonic wedge for transmitting or receiving the ultrasonic signal which is generated or received from the ultrasonic signal generator, and wherein the ultrasonic wedge is slidably borne by the carriage and moves in unison along the path travel with each of the ultrasonic signal generator or receiver, and wherein the ultrasonic wedge is formed of first and second materials having different acoustic properties, and wherein the first material is imbedded at a predetermined angle in the second material, and wherein the first material transmits or receives the ultrasonic signal which is generated by the ultrasonic signal generator, and wherein the first material receives the ultrasonic signal which travels along an incident angle which remains substantially constant with increasing temperature; and a controller electrically coupled with the ultrasonic signal generator and ultrasonic signal receiver to initiate the generation of ultrasonic signals, process the ultrasonic signal received by the ultrasonic signal receiver, and with each propulsion assembly to coordinate the movement of the ultrasonic signal generator and receiver relative to the opposite sides of the partially completed weld.

24. An apparatus for the concurrent inspection of partially completed welds, comprising:
- a moveable welder for forming a partially completed weld; and
- an ultrasonic generator mounted on the moveable welder, and which produces a signal with an incident angle that is independent of temperature.

25. An apparatus for the concurrent inspection of partially completed welds, comprising:
- a moveable welder for forming a partially completed weld;
- an ultrasonic generator mounted on the moveable welder which produces an ultrasonic signal; and
- an ultrasonic wedge for receiving the ultrasonic signal produced by the ultrasonic generator, and which transmits the ultrasonic signal along an incident angle that is independent of temperature.

26. An apparatus for the concurrent inspection of partially completed welds, comprising:
- a moveable welder for forming a partially completed weld on a substrate;
- an ultrasonic generator mounted on the moveable welder, and which produces an ultrasonic signal; and
- an ultrasonic wedge disposed in ultrasonic signal receiving relation relative to the ultrasonic generator, and which transmits the ultrasonic signal along an incident angle that is independent of temperature to an underlying substrate which is being concurrently welded by the moveable welder.

27. An apparatus for the concurrent inspection of partially completed welds, comprising:
- a moveable welder for forming a partially completed weld;
- an ultrasonic generator mounted on the moveable welder for generating ultrasonic signals; and
- an ultrasonic wedge for receiving the ultrasonic signals, and which has first and second materials, and wherein the second material has an ultrasonic attenuation which is large in relative comparison to the first material.

28. An apparatus for the concurrent inspection of partially completed welds, comprising:
- a moveable welder for forming a partially completed weld;
- an ultrasonic generator mounted on the moveable welder for generating ultrasonic signals; and
- an ultrasonic wedge formed from a first an second material which each have a predetermined ultrasonic impedance and attenuation, and which receives the ultrasonic signal, and wherein the acoustic impedance of the first and second materials are substantially similar, and the ultrasonic attenuation of the second material is large in relative comparison to the first material.

* * * * *